United States Patent
Rickheim et al.

(10) Patent No.: US 12,000,448 B2
(45) Date of Patent: Jun. 4, 2024

(54) BIOSTIMULATOR TRANSPORT SYSTEM HAVING TORQUE LIMITER

(71) Applicant: Pacesetter, Inc., Sylmar, CA (US)

(72) Inventors: David Rickheim, Bloomington, MN (US); Scott Kerns, Chanhassen, MN (US); Daniel Coyle, Saint Louis Park, MN (US)

(73) Assignee: PACESETTER, INC., Sylmar, CA (US)

( * ) Notice: Subject to any disclaimer, the term of this patent is extended or adjusted under 35 U.S.C. 154(b) by 902 days.

(21) Appl. No.: 17/018,689

(22) Filed: Sep. 11, 2020

(65) Prior Publication Data

US 2021/0085990 A1     Mar. 25, 2021

Related U.S. Application Data

(60) Provisional application No. 62/903,487, filed on Sep. 20, 2019.

(51) Int. Cl.
    *F16D 7/04*     (2006.01)
    *A61N 1/05*     (2006.01)
    (Continued)

(52) U.S. Cl.
CPC ............... *F16D 7/04* (2013.01); *A61N 1/372* (2013.01); *A61N 1/37518* (2017.08);
(Continued)

(58) Field of Classification Search
CPC .......... A61M 25/0082; A61M 25/0113; A61N 1/372; A61N 1/37518; A61N 1/3756; A61N 2001/0578; A61N 2001/058; F16C 1/02; F16C 1/04; F16C 1/06; F16C 1/08; F16D 7/00; F16D 7/002; F16D 7/04;
(Continued)

(56) References Cited

U.S. PATENT DOCUMENTS

| | | | | |
|---|---|---|---|---|
| 2,143,710 A | * | 1/1939 | Murray | F16D 35/00 475/94 |
| 4,610,340 A | * | 9/1986 | Helmes | F16D 7/048 464/35 |

(Continued)

FOREIGN PATENT DOCUMENTS

| | | |
|---|---|---|
| DE | 2853900 A1 * | 6/1980 |
| DE | 3335729 A1 * | 4/1985 |

(Continued)

*Primary Examiner* — Josh Skroupa
(74) *Attorney, Agent, or Firm* — WOMBLE BOND DICKINSON (US) LLP

(57) ABSTRACT

A biostimulator transport system, such as a biostimulator retrieval system, having a torque limiter to allow a torque shaft to slip rotationally relative to a handle, is described. The torque limiter can connect the torque shaft to the handle, and can include a slip mechanism, such as a flat spring or apposed clutch faces, that allow the torque shaft to slip relative to the handle when a resistance torque at a distal end of the torque shaft exceeds a torque threshold. Accordingly, torque can be applied to a biostimulator by the torque shaft with a reduced likelihood of over-torqueing the biostimulator within the target tissue. Other embodiments are also described and claimed.

20 Claims, 13 Drawing Sheets

(51) Int. Cl.
*A61N 1/372* (2006.01)
*A61N 1/375* (2006.01)

(52) U.S. Cl.
CPC *A61N 2001/0578* (2013.01); *A61N 2001/058* (2013.01); *A61N 1/3756* (2013.01)

(58) Field of Classification Search
CPC ........ F16D 7/048; F16D 43/20; F16D 43/202; F16D 43/2028
USPC ..................................................... 464/30, 37
See application file for complete search history.

(56) References Cited

U.S. PATENT DOCUMENTS

| | | | | |
|---|---|---|---|---|
| 5,020,648 | A * | 6/1991 | Bush | F16D 7/048 192/64 |
| 7,533,474 | B2 * | 5/2009 | Saito | F16D 7/048 33/783 |
| 8,313,384 | B2 * | 11/2012 | Yang | F16D 7/002 464/37 |
| 10,272,501 | B2 * | 4/2019 | Wagner | F16D 19/00 |
| 10,865,061 | B2 * | 12/2020 | Amemiya | F16D 7/048 |
| 11,441,611 | B2 * | 9/2022 | Leung | F16D 7/002 |
| 2005/0006832 | A1 * | 1/2005 | Hoshi | F16D 7/048 267/154 |

FOREIGN PATENT DOCUMENTS

| | | | | |
|---|---|---|---|---|
| DE | | 10311367 | A1 * | 10/2003 |
| DE | 102011075291 | A1 * | 3/2012 |
| FR | | 979068 | A * | 4/1951 |

* cited by examiner

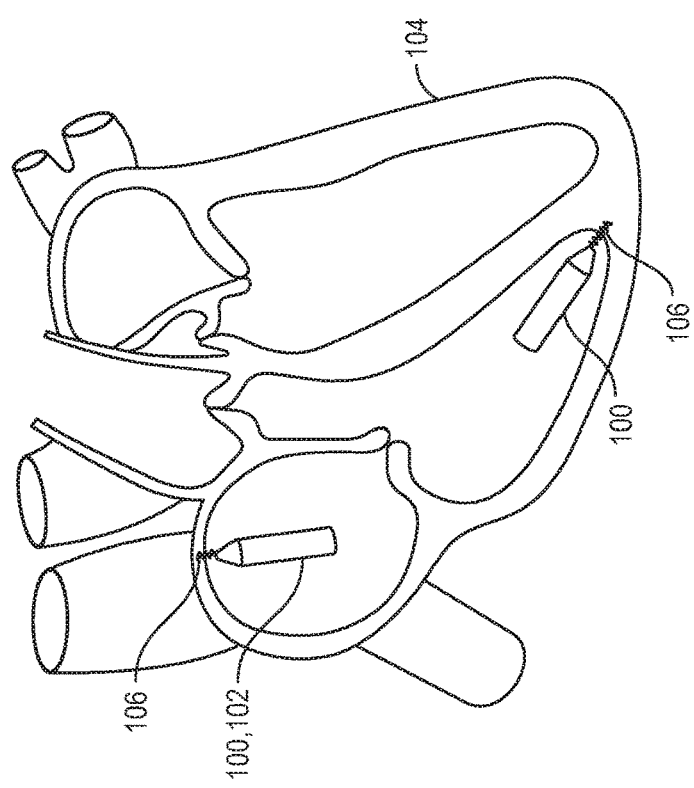
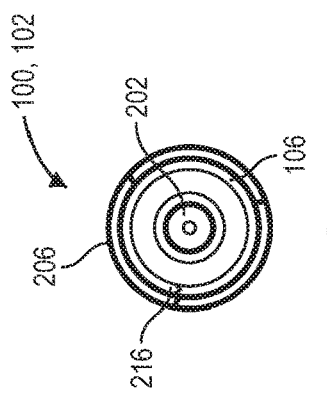
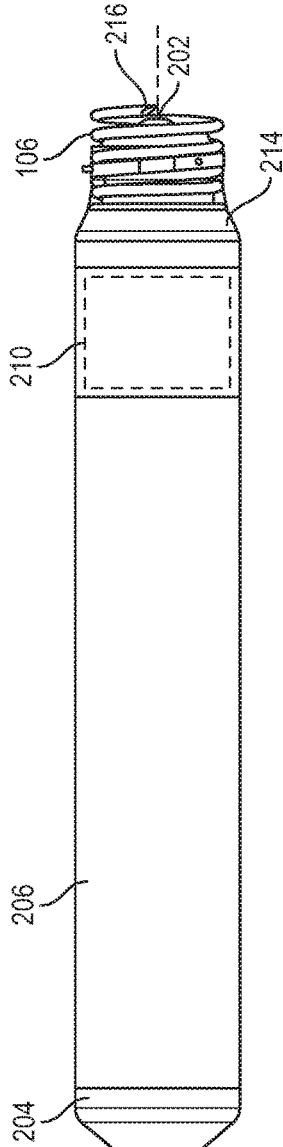
FIG. 1
FIG. 2A
FIG. 2B

BIOSTIMULATOR TRANSPORT SYSTEM HAVING TORQUE LIMITER

This application claims the benefit of priority of U.S. Provisional Patent Application No. 62/903,487, filed Sep. 20, 2019, entitled "Biostimulator Transport System Having Torque Limiter," and that patent application is incorporated herein by reference in its entirety to provide continuity of disclosure.

BACKGROUND

Field

The present disclosure relates to biostimulators and related delivery and retrieval systems and methods. More specifically, the present disclosure relates to transport systems for delivery or retrieval of leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The generator usually connects to a proximal end of one or more implanted leads, the distal end of which contains one or more electrodes for positioning adjacent to the inside or outside wall of a cardiac chamber. Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

Leadless cardiac pacemakers incorporate electronic circuitry at the pacing site and eliminate leads, and thus, avoid the above-mentioned shortcomings of conventional cardiac pacing systems. Leadless cardiac pacemakers can be anchored at the pacing site by an anchor. During delivery or retrieval of a leadless cardiac pacemaker, a transport system can apply torque to the leadless cardiac pacemaker via a docking cap to screw the anchor into, or out of, the target tissue.

SUMMARY

Existing transport systems include biostimulator delivery systems, which tether the biostimulator to the docking cap, navigate through a patient to a target tissue, screw the biostimulator into the target tissue, and undock the biostimulator to remain at the target tissue. Existing transport systems also include biostimulator retrieval systems, which snare the implanted biostimulator, retract the biostimulator into the docking cap, unscrew the biostimulator from the target tissue, and remove the biostimulator from the patient. While the biostimulator is implanted, tissue ingrowth can occur. The longer that the biostimulator remains implanted, the more tissue ingrowth may occur, and thus, the more torque may be required to unscrew the biostimulator from the target tissue. The required removal torque may be so high that, when the torque is input to a torque transmission component, e.g., via a handle, the input torque can damage the biostimulator transport system. Furthermore, the high torque may place undue stress on the target tissue, and thus, can lead to injury.

A biostimulator transport system that decouples the torque input from the torque output under certain circumstances, is provided. The biostimulator transport system can be a catheter-based system for delivering or retrieving a leadless pacemaker. The biostimulator transport system can include a torque limiter to allow a torque shaft to slip relative to a handle based on a resistance torque applied to the torque shaft. In an embodiment, the biostimulator transport system includes a torque shaft assembly having a docking cap, the torque shaft coupled to the docking cap, and the torque limiter. The torque limiter can include a torque puck mounted on the torque shaft, and a torque shuttle that is rotationally coupled to the torque puck. More particularly, a slip mechanism can be between the torque puck and the torque shuttle, and can connect the components rotationally. The torque shuttle can be coupled to a handle and can transmit torque to the torque puck through the slip mechanism when a resistance torque at the docking cap is below a torque threshold. When the resistance torque is below the threshold, the torque puck and the torque shuttle can rotate together. When the resistance torque exceeds the torque threshold, the slip mechanism allows the torque puck to slip rotationally relative to the torque shuttle to release built up torque in the system.

The slip mechanism can include a flat spring that is fixed to one of the torque puck or the torque shuttle. The flat spring can engage a groove in the other of the torque puck or the torque shuttle. For example, the torque puck can have radial teeth that define the groove therebetween. The flat spring can rest within the groove to transmit torque between the torque shuttle and the torque puck until the torque threshold is exceeded. When the torque threshold is exceeded, the flat spring can ratchet to a next groove in the torque puck, thereby releasing pent up torque and avoiding excessive torque build up in the system.

The slip mechanism can include an inner shuttle containing the torque puck. The inner shuttle can be contained within the torque shuttle, and can have an inner clutch face apposed to an outer clutch face of the torque shuttle. The slip mechanism can include a bias element that forces the clutch faces together. The clutch faces form a clutch interface at which friction is generated. The friction resists relative rotation between the clutch faces, and thus, between the torque shuttle and the inner shuttle. Accordingly, the torque shuttle can transmit torque to the inner shuttle and the torque puck via the clutching mechanism until the threshold torque is exceeded. When the threshold torque is exceeded, the inner shuttle can slip relative to the torque shuttle at the clutch interface, thereby releasing pent up torque and avoiding excessive torque build up in the system.

Alternative slip mechanisms are contemplated and described. For example, the slip mechanism can include a ball plunger connecting the torque shuttle to the torque puck. In an embodiment, the slip mechanism includes a shear pin connecting the torque shuttle to the torque puck. In each embodiment, the slip mechanism can constrain rotational movement between the torque shuttle and the torque puck based on the resistance torque to allow the components to slip when necessary to avoid system damage due to excessive torque build up.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is a diagrammatic medial-lateral cross section of a patient heart illustrating an example implantation of biostimulators in the patient heart, in accordance with an embodiment.

FIGS. 2A-2B are, respectively, side and end views of a biostimulator, in accordance with an embodiment.

DETAILED DESCRIPTION

Figure 3A:
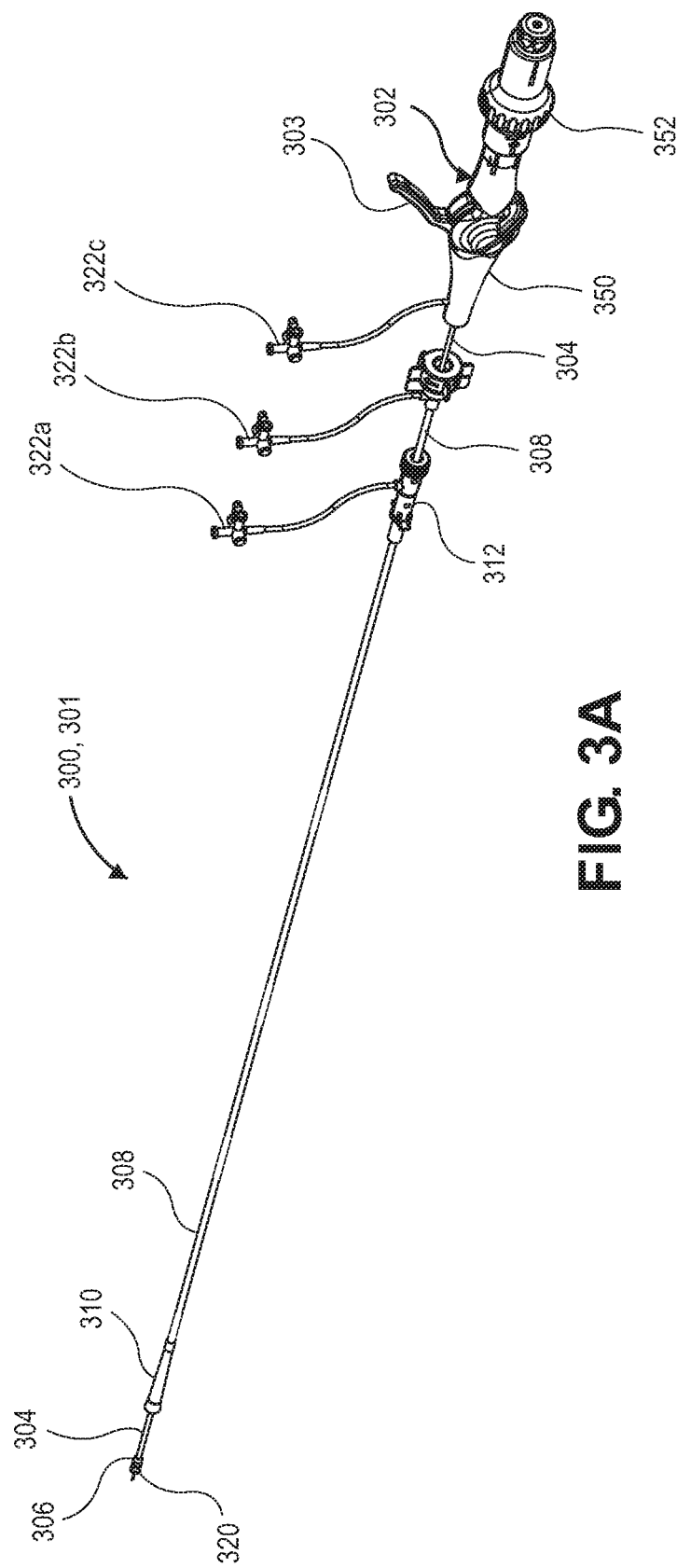
FIGS. 3A-3B are perspective views of a biostimulator delivery system, in accordance with an embodiment.

Embodiments describe a biostimulator transport system, such as a biostimulator retrieval system, having a torque limiter. The biostimulator transport system can be used to deliver or retrieve a biostimulator from a heart of a patient. The biostimulator may, however, be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a central axis of a biostimulator transport system. Similarly, "proximal" may indicate a second direction opposite to the first direction. Such terms are provided to establish relative frames of reference, however, and are not intended to limit the use or orientation of a biostimulator transport system to a specific configuration described in the various embodiments below.

In an aspect, a biostimulator transport system has a torque limiter to allow a torque shaft to slip rotationally relative to a handle. The torque limiter can include an input portion, such as a shuttle that is rotationally fixed relative to the handle, and an output portion, such as a torque puck mounted on the torque shaft. A slip mechanism connects the input portion to the output portion and allows the portions to slip relative to each other when a torque threshold is met. Accordingly, the torque shaft can slip relative to the housing to reduce a likelihood that excessive torque will be built up in the system, and thus, reduce a likelihood of causing tissue injury while screwing a biostimulator into or out of the tissue by the torque shaft.

Referring to FIG. 1, a diagrammatic medial-lateral cross section of a patient heart illustrating an example implantation of biostimulator in the patient heart is shown in accordance with an embodiment. A cardiac pacing system includes one or more biostimulators 100. The biostimulator(s) 100 can be implanted at respective target sites in a patient heart 104. The biostimulator(s) 100 can be leadless, and thus, may be leadless cardiac pacemakers 102. Each biostimulator 100 can be placed in a cardiac chamber, such as a right atrium and/or right ventricle of the patient heart 104, or attached to an inside or outside of the cardiac chamber. Attachment of the biostimulator 100 to the target tissue can be accomplished via one or more fixation elements 106, such as helical anchors. In a particular embodiment, the leadless pacemaker can use two or more electrodes located on or within a housing of the leadless pacemaker for pacing the cardiac chamber upon receiving a triggering signal from internal circuitry and/or from at least one other device within the body.

Referring to FIG. 2A, a side view of a biostimulator is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes, e.g., a distal electrode 202 and a proximal electrode 204, located within, on, or near a housing 206 of the biostimulator 100. In an embodiment, the fixation element 106 forms a portion of the distal electrode 202. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example, bidirectional communication. The housing 206 can optionally contain an electronics compartment 210 to hold circuitry adapted for different functionality. For example, the electronics compartment 210 can contain circuits for sensing cardiac activity from the electrodes, circuits for receiving information from at least one other device via the electrodes, circuits for generating pacing pulses for delivery via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanisms or fixation mechanisms, such as a screw or helical member that screws into the myocardium. In an embodiment, the biostimulator 100 includes the fixation element 106 coupled to the housing 206. The fixation element 106 can be a helical element to screw into target tissue. More particularly, the fixation element 106 can extend helically from a flange 214 of the biostimulator 100, which is mounted on the housing 206, to a distal tip at a helix distal end 216.

In an embodiment, the biostimulator 100 includes an attachment feature 218. The attachment feature 218 can be, for example, a protuberance extending proximally from the housing 206. As described below, the attachment feature 218 can have a shape and size that meshes with a corresponding component of a biostimulator transport system. For example, a distal end of the biostimulator transport system can receive the attachment feature 218, and transmit torque to the biostimulator through the attachment feature 218. Accordingly, the attachment feature 218 allows the biostimulator 100 to be captured and manipulated by the biostimulator transport system.

Referring to FIG. 2B, an end view of a biostimulator is shown in accordance with an embodiment. The helix distal end 216 can be located distal to the distal electrode 202 (a centrally located electrode). Accordingly, when the biostimulator 100 contacts the target tissue, the distal tip can pierce the tissue and the housing 206 can be rotated in a first direction, e.g., clockwise, to screw the fixation element 106 into the target tissue to pull the distal electrode 202 into contact with the tissue. By contrast, the housing 206 can be rotated in a second direction, e.g., counterclockwise, to unscrew the fixation element 106 from the target tissue to retrieve the biostimulator 100.

Leadless pacemakers or other leadless biostimulators 100 can be delivered to and retrieved from a patient using a transport system, as described below. In some implementations, the transport system is a delivery system for delivering the leadless pacemaker to the target tissue. In some implementations, the transport system is a retrieval system for retrieving the leadless pacemaker from the target tissue. Such delivery systems and retrieval systems can incorporate components in common, such as a torque shaft, a torque shaft assembly, or a torque limiter, as described below.

Referring to FIG. 3A, a perspective view of a biostimulator transport system is shown in accordance with an embodiment. A biostimulator transport system 300 may be used for delivery and/or retrieval of the biostimulator 100, e.g., a leadless pacemaker, into or from a patient. For example, the biostimulator transport system can be a biostimulator delivery system 301 used for delivery of the biostimulator 100 into a patient.

The biostimulator transport system 300 can include a handle 302, and an elongated catheter 304 extending distally from the handle 302 to a distal catheter end 306. The handle 302 can include several portions, e.g., a distal handle portion 350 and a proximal handle portion 352, and features that allow a user to provide inputs at a proximal end of the system that translate to outputs at the distal end of the system. For example, the elongated catheter 304 can be a deflectable catheter, and an operator can use the handle 302 to steer the distal catheter end 306 in the patient.

In an embodiment, the handle 302 includes a deflection lever 303 that can be used to deflect the distal catheter end 306. By pivoting the deflection lever 303 toward a distal handle portion 350 of the handle 302, the operator can cause a pull ring assembly extending within the elongated catheter 304 to apply off-axis compression to the elongated catheter 304, resulting in lateral deflection of the distal catheter end 306.

The handle 302 can be used to apply a torque to a docking cap 320 at the distal end of the system. In an embodiment, the proximal handle portion 352 can be rotationally and/or longitudinally moveable relative to the distal handle portion 350. For example, the distal handle portion 350 can be coupled to the elongated catheter 304 and the proximal handle portion 352 can be coupled to a torque shaft extending within the elongated catheter 304. The docking cap 320 can be mounted on the torque shaft. Accordingly, an operator can rotate the proximal handle portion 352 relative to the distal handle portion 350 to impart torque to the torque shaft. The torque can cause the docking cap 320, which is rotationally linked to the proximal handle portion 352 through the torque shaft to rotate relative to the elongated catheter 304, which is rotationally linked to the distal handle portion 350.

In an embodiment, the biostimulator transport system 300 includes a protective sheath 308 mounted on the elongated catheter 304. The protective sheath 308 can be slidably disposed on the elongated catheter 304. The protective sheath 308 can include an atraumatic end 310, e.g., a soft, funnel-shaped distal portion, that can slide distally over the distal catheter end 306 of the elongated catheter 304 and/or the biostimulator 100 (not shown). The atraumatic end 310 can have an outer dimension, which may be larger than a proximal portion of the protective sheath 308. For example, the atraumatic end 310 may flare in a distal direction to a funnel opening that can advance over a docking cap 320 of the biostimulator transport system 300. An outer dimension of the atraumatic end 310 can be larger than a region of the protective sheath 308 supporting a valve bypass tool 312.

The valve bypass tool 312 can be slidably disposed on the protective sheath 308 such that a distal portion of the valve bypass tool 312 can slide distally over the distal catheter end 306 of the elongated catheter 304 and/or the atraumatic end 310 of the protective sheath 308. More particularly, the valve bypass tool 312 can be inserted into an access introducer to gain access to the patient vasculature, and after access is established, the distal portion of the protective sheath 308 and/or the distal end of the elongated catheter 304 can be advanced through the valve bypass tool 312 into the patient.

The valve bypass tool 312, the protective sheath 308, and the elongated catheter 304 can have respective flush ports 322a, 322b, and 322c extending respectively therefrom. Each of the longitudinal bodies are displaceable proximal-distal relative to each other, and thus, the flush ports can be used to introduce and/or flush saline or other fluids between the longitudinal bodies or through the respective components in different relative positions.

Figure 3B:
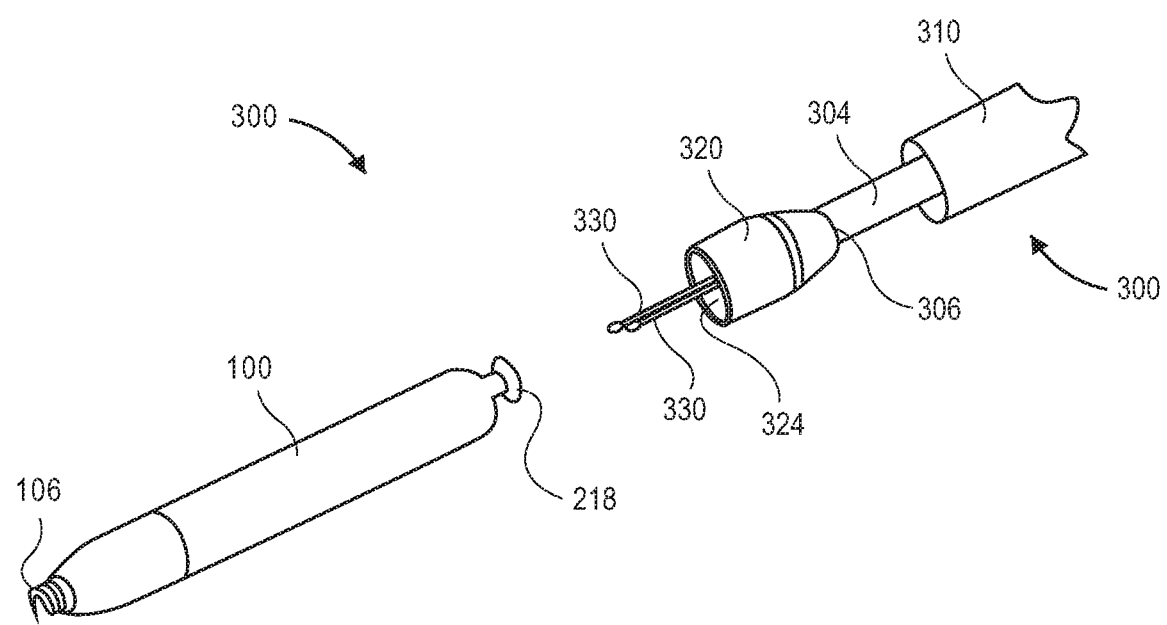

Referring to FIG. 3B, a distal perspective view of a biostimulator transport system having a docking cap to receive a biostimulator is shown in accordance with an embodiment. The distal catheter end 306 of the elongated catheter 304 may be selectively connectable to the biostimulator 100. More particularly, the biostimulator 100 can be mounted on the distal catheter end 306 of the elongated catheter 304. In an embodiment, the attachment feature 218 includes a channel (not shown) shaped and sized to receive one or more tethers 330. The tethers 330 can comprise wires, shafts, tubes, cords, ropes, strings, or other similar structures that can extend throughout the catheter shaft 304. For example, the tethers 330 can extend through a shaft lumen of a torque shaft assembly. In some embodiments, the tethers 330 comprise a shape memory material, such as nickel-titanium. In other embodiments, the tethers 330 comprise stainless steel wires or braids. The tethers 330 can be inserted into and locked within the attachment feature 218 to connect the biostimulator 100 to the biostimulator transport system 300.

When the tethers 330 are locked within the attachment feature 218, the tethers 330 can be retracted to pull the biostimulator 100 toward the docking cap 320. The docking cap 320 can include a docking cavity 324 having a shape and size to receive the attachment feature 218 of the biostimulator 100. As the biostimulator 100 moves toward the docking cap 320, the attachment feature 218 can insert into the docking cavity 324. Accordingly, the docking cavity 324 can receive the attachment feature 218 to dock the biostimulator 100 to the biostimulator transport system 300 for delivery to the patient.

Torque can be transmitted from the docking cap 320 to the biostimulator 100 via the torque shaft when the attachment feature 218 is received in the docking cap 320. More particularly, the torque shaft can be rotated in a first direction, e.g., clockwise, to transmit torque through the docking cap 320 to the attachment feature 218, and to cause the fixation element 106 to engage and screw into the heart tissue.

The biostimulator 100 can be protected by the atraumatic end 310 of the protective sheath 308 during delivery and/or retrieval of the biostimulator 100 from the patient. The atraumatic end 310 can have a braided or woven tubular construction. The atraumatic end 310 can therefore be advanced over the biostimulator 100 and may expand radially over the biostimulator 100 in the case where an outer dimension of the biostimulator 100 is greater than the inner diameter of the atraumatic end 310. Accordingly, the atraumatic end 310 can cover the biostimulator 100 to protect the biostimulator during advancement into the patient.

Figure 4A:
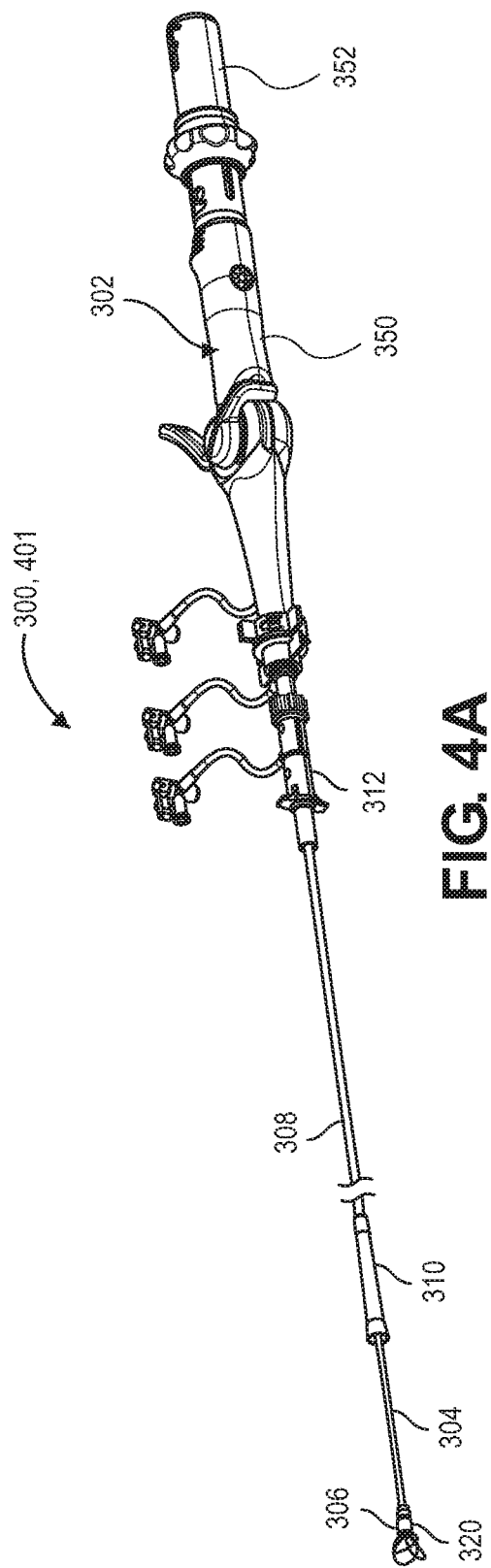
FIGS. 4A-4B are perspective views of a biostimulator retrieval system, in accordance with an embodiment.

Referring to FIG. 4A, a perspective view of a biostimulator retrieval system is shown in accordance with an embodiment. The biostimulator transport system 300 may be a biostimulator retrieval system 401. The biostimulator retrieval system 401 can be used to explant one or more biostimulator 100 from the atrium and/or the ventricle of the heart of the patient. Removal and retrieval of the biostimulator(s) 100 may be accomplished endocardially. For example, the torque shaft of the elongated catheter 304 can be rotated in a second direction, e.g., counterclockwise, to disengage the biostimulator 100 from the heart tissue. Accordingly, retrieval system 401 shown in FIG. 4A can have a structure similar to that shown and described with respect to the delivery system of FIG. 3A to retrieve the biostimulator 100 from a target anatomy. The similarly numbered components of the biostimulator retrieval system 401 and not described again here for brevity.

Figure 4B:
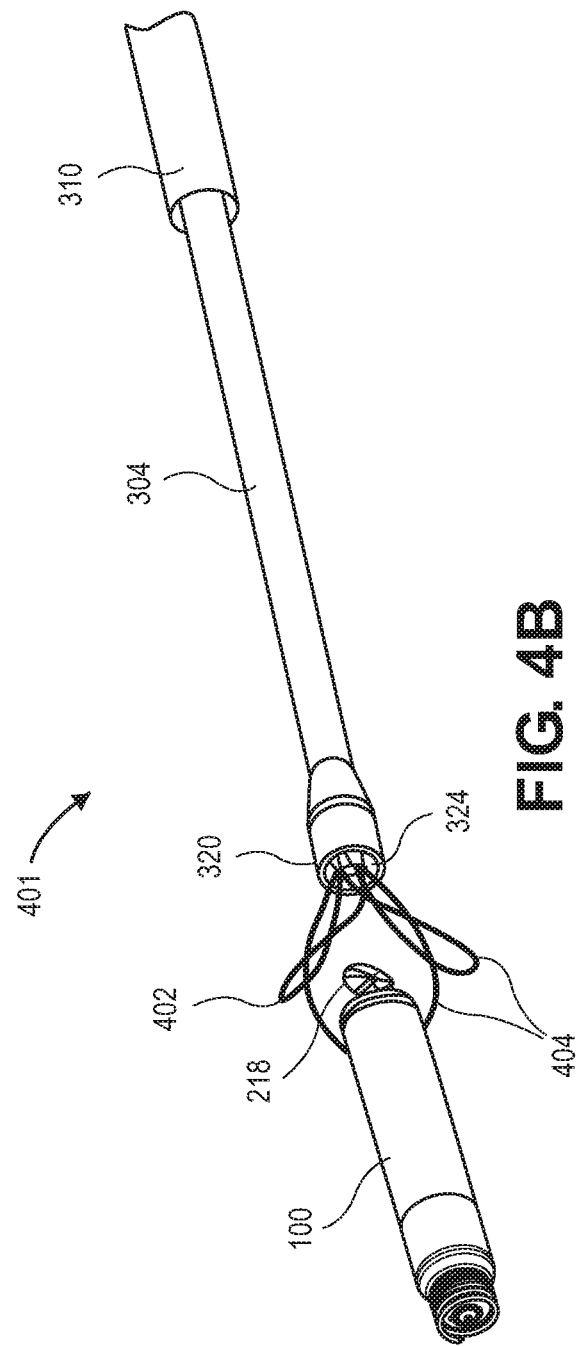

Referring to FIG. 4B, a perspective view of a distal portion of a biostimulator retrieval system prior to attaching to a biostimulator is shown in accordance with an embodiment. The distal portion of the biostimulator transport system 300 can include features to engage the leadless pacemaker to facilitate capturing and unscrewing the biostimulator 100 from the target tissue. More particularly, the biostimulator retrieval system 401 can include a snare 402 extending through the elongated catheter 304 to grasp a biostimulator 100 or other medical device. The snare 402 can include at least one snare loop 404, e.g., a wire loop, extending from the elongated catheter 304. As the snare 402 is advanced distally out of the biostimulator transport system 300 from the docking cap 320, the loop(s) 404 can expand in size to aid a user in positioning the snare 402 around or in proximity to the biostimulator 100 to be retrieved. In some implementations, as in FIG. 4B, the snare 402 can include multiple loops 404, such as three loops. However, any number of loops can be used as long as the elongated catheter 304 contains sufficient volume to accommodate the loops.

The distal portion of the retrieval catheter can include the docking cap 320 configured to allow docking of the leadless pacemaker with the biostimulator transport system 300 after engaging the pacemaker with the snare 402. A user can transmit torque through the torque shaft via handle 302 to rotate the docking cap 320 relative to the elongated catheter 304. More particularly, the torque shaft can extend through the length of the catheter to the handle 302, e.g., the proximal handle portion 352, which is coupled to the torque shaft. Rotation or actuation of the handle 302 rotates the torque shaft, thereby rotating the docking cap 320 at the end of the retrieval catheter. The protective sheath 308 can be positioned along the elongated catheter 304, and can be advanced or retracted to cover or expose the docking cap 320 and the leadless pacemaker 100 using the atraumatic end 310.

During retrieval, the biostimulator transport system 300 can be navigated through the patient to the implant site. The snare 402 can be placed over the attachment feature 218 and the loops of the snare 420 can be reduced in size, thereby grasping or locking onto the attachment feature 218 of the pacemaker. Following capture and locking of the snare 402 with the leadless pacemaker, the biostimulator 100 may be docked within the docking cap 320. More particularly, the attachment feature 218 of the biostimulator 100 can be pulled into a docking cavity 324 of the docking cap 320. In some implementations, the docking cap 320 can include a key or interference feature configured to mate with and engage a corresponding key or feature on the pacemaker. In some implementations, the key or slot on the docking cap 320 can match a unique shape or feature of the attachment feature 218 of the pacemaker. Because the key or slot on or in the docking cap 320 can mate with and engage the key or slot on the pacemaker, the retrieval catheter can be configured to apply torque to the pacemaker to unscrew and remove the pacemaker from tissue.

When torque is transmitted to the biostimulator 100 by the biostimulator transport system 300 during delivery or retrieval, torque can build up in the system when there is a resistance torque at the docking cap 320. For example, when the biostimulator 100 is embedded in the target tissue, and tissue has grown around the housing 206, the tissue ingrowth can resist torque applied to the biostimulator 100 by the docking cap 320, and thus, torque can become stored in the torque shaft assembly. The stored torque can act on the system components, such as the bonds between the torque shaft and the docking cap 320, for example. Excessive torque can cause failure of such bonds. Accordingly, the biostimulator transport system 300 can incorporate a torque limiter to limit the torque built up in the system, and thus, reduce a likelihood of system failure due to exceeding the ultimate torque strength of the catheter components and/or component interfaces.

Figure 5:
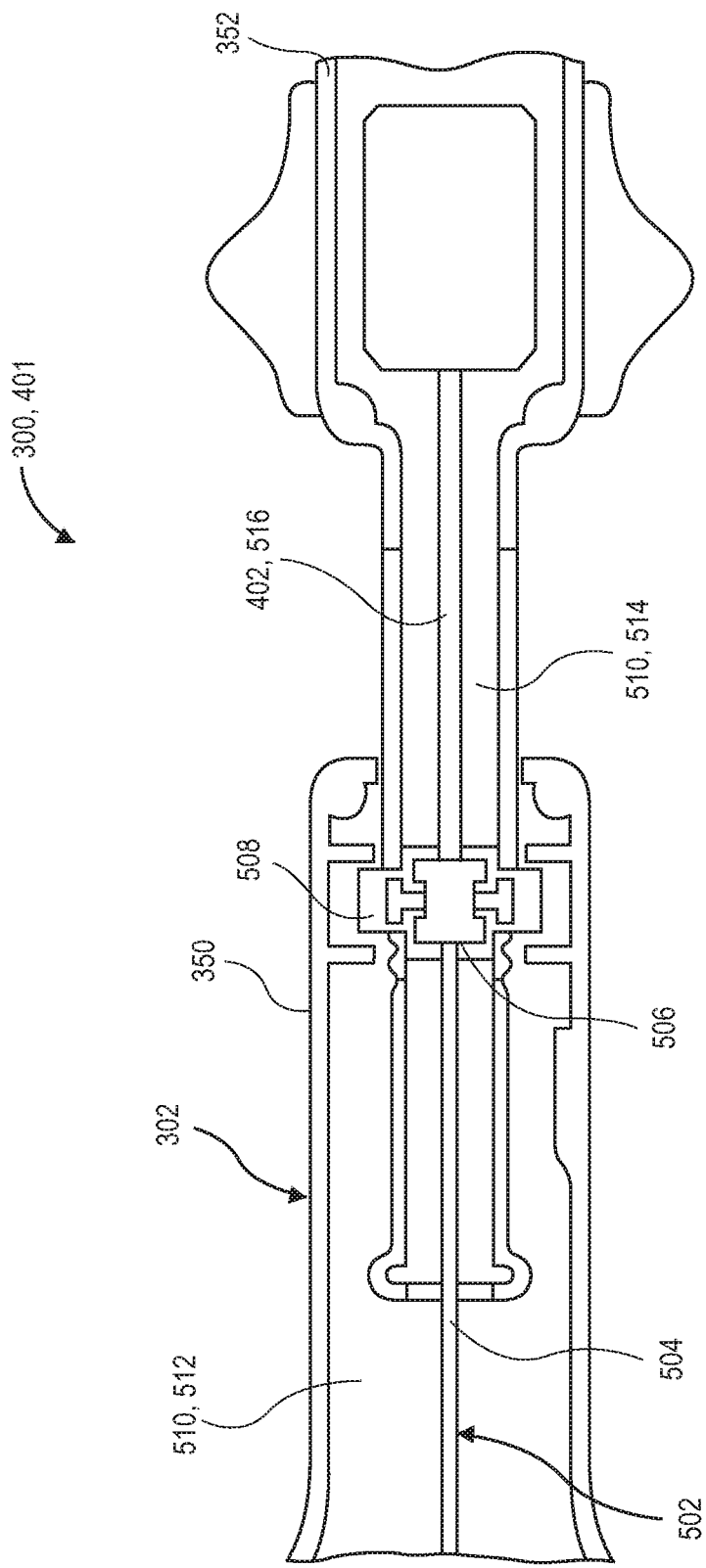
FIG. 5 is a cross-sectional side view of a biostimulator transport system handle, in accordance with an embodiment.

Referring to FIG. 5, a cross-sectional side view of a biostimulator transport system handle is shown in accordance with an embodiment. The biostimulator transport system 300 can include a torque shaft assembly 502. The torque shaft assembly 502 includes the docking cap 320, as described above, and a torque shaft 504 connected to the docking cap 320. More particularly, the torque shaft 504 can have a distal shaft end (not shown) that attaches to the docking cap 320 within the distal end of the elongated catheter 304. The distal shaft end can be attached to the docking cap 320 by a weld, an adhesive bond, etc. Whereas the distal shaft end can be distal to the handle 302, the torque shaft 504 may include a proximal shaft end 506 contained within the handle 302. For example, the torque shaft assembly 502 can include a torque limiter 508 that is contained within a handle cavity 510 of the handle 302, and the proximal shaft end 506 may be attached to the torque limiter 508 in the handle cavity 510.

The torque limiter 508 can be mounted on the torque shaft 504 in the handle cavity 510. The distal handle portion 350 can include a distal handle cavity 512, and the proximal handle portion 352 can include a proximal handle cavity 514. The handle portions may be thin-walled shells, and thus, the respective handle cavities can have inner handle surfaces that are offset from respective outer handle surfaces by a thickness of the handle walls. The inner handle surfaces define the respective cavities. For example, the inner handle surface of the distal handle portion 350 defines the distal handle cavity 512 within the distal handle portion 350, and the inner handle surface of the proximal handle portion 352 defines the proximal handle cavity 514 within the proximal handle portion 352. The torque limiter 508 may be contained within distal handle cavity 512 and the proximal handle cavity 514.

In an embodiment, the biostimulator transport system 300 is the biostimulator retrieval system 401. In such case, the biostimulator transport system 300 includes the snare 402 extending through the torque shaft 504 and the torque limiter 508. More particularly, the torque shaft 504, which may be coupled to the docking cap 320, can include a shaft lumen extending from the proximal shaft and within the torque limiter 508 to the distal shaft end attached to the docking cap 320. In an embodiment, a snare tube 516 of the snare 402 can extend through the torque limiter 508 and the shaft lumen from the proximal handle portion 352 to the docking cap 320. More particularly, the snare tube 516 can be longitudinally movable within the shaft lumen and can be advanced or retracted within the shaft lumen. The snare tube 516 can have a central lumen that the one or more snare loops 404 extend through. Furthermore, the snare tube 516 may be longitudinally movable relative to the snare loops 404. Accordingly, the snare tube 516 can be advanced over the snare loops 404 within the shaft lumen to cinch the snare loops 404, or alternatively, the snare tube 516 can be retracted over the snare loops 404 within the shaft lumen to allow the snare loops 404 to expand. The snare loop actuation allows the snare 402 to capture the biostimulator 100, as described above.

Figure 6:
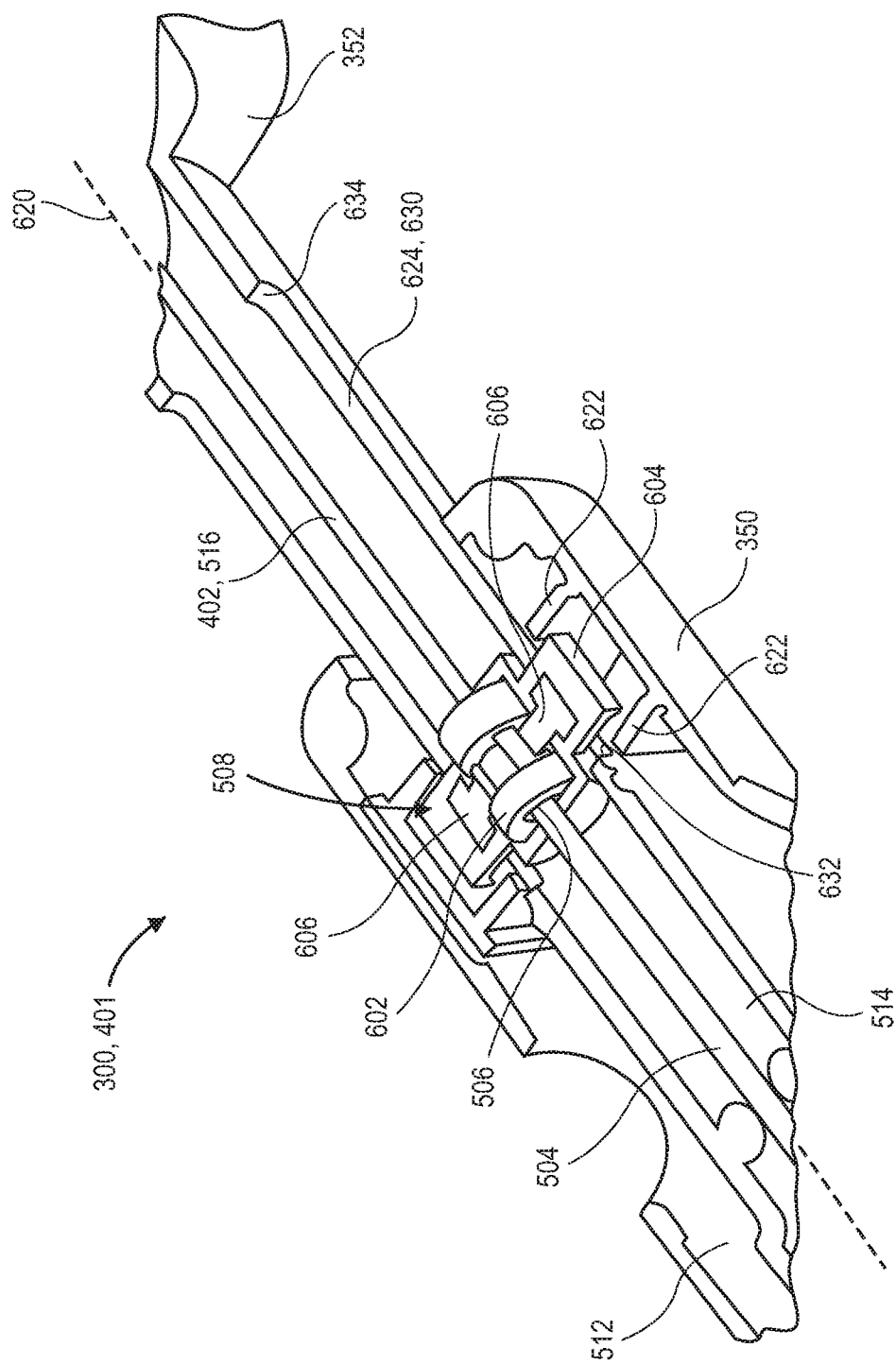
FIG. 6 is a cross-sectional perspective view of a biostimulator transport system handle, in accordance with an embodiment.

Referring to FIG. 6, a cross-sectional perspective view of a biostimulator transport system handle is shown in accordance with an embodiment. The torque limiter 508 can include several components that are capable of moving relative to each other. In an embodiment, the torque limiter 508 includes a torque puck 602, which can be mounted on the torque shaft 504. More particularly, the torque puck 602 can be attached to the proximal shaft end 506 of the torque shaft 504. The torque puck 602 may be fixed to the torque shaft, e.g., by a weld, an adhesive bond, etc. Accordingly, a torque applied to the torque puck 602 can be transmitted to the torque shaft 504, and vice versa.

The torque limiter 508 can include a torque shuttle 604, which may be rotationally coupled to the torque puck 602. More particularly, the torque puck 602 can be contained within the torque shuttle 604 such that the torque puck 602 can rotate relative to the torque shuttle 604 under certain conditions. Relative rotation between the torque puck 602 and the torque shuttle 604 may be modulated by a slip mechanism 606. The slip mechanism 606 can be a component of the torque limiter 508 that is coupled to the torque puck 602 and the torque shuttle 604. More particularly, the slip mechanism 606 can be between the torque puck 602 and the torque shuttle 604 to allow the torque puck 602 to slip, e.g., rotationally, relative to the torque shuttle 604 based on a resistance torque on the torque shaft 504. This torque limiting function of the torque limiter 508 is described further below.

Notably, the torque limiter 508 can have a channel extending through the torque shuttle 604 and the torque puck 602 along a central axis 620 of the biostimulator transport system 300. When the biostimulator transport system 300 is the biostimulator retrieval system 401 having the snare 402, the central axis 620 can extend through the snare 402, the torque shaft 504, and the docking cap 320. Accordingly, a portion of the snare 402, e.g., the snare tube 516 or a snare wire (not shown) attached to the snare loops 404 within the snare tube 516, can extend distally from the proximal handle portion 352 through the torque puck 602, the torque shaft 504, and the docking cap 320. The snare tube 516 can advance or retract to actuate the snare loops 404 within a patient.

Several embodiments of the torque limiter 508 are described below. In each embodiment, the torque shaft 504 can be coupled to and/or fixed relative to the torque puck 602 in a rotational and longitudinal direction relative to the central axis 620 of the biostimulator transport system 300. Furthermore, the torque puck 602 can be longitudinally constrained relative to the torque shuttle 604, and thus, the torque shaft 504 can be longitudinally constrained relative to the torque shuttle 604. Accordingly, when the torque shaft 504 is placed in compression, it does not move axially relative to the torque limiter 508. The torque puck 602 may, however, move rotationally relative to the torque shuttle 604 when the slip mechanism 606 slips, and thus, the torque shaft 504 can be rotationally constrained relative to the torque shuttle 604 by the slip mechanism 606.

In an embodiment, the torque limiter 508, the components of which are constrained relative to the torque shaft 504, is also constrained relative to the distal handle portion 350 and the proximal handle portion 352. As described above, the torque limiter 508, and thus the torque shuttle 604, can be contained within the distal handle cavity 512 of the distal handle portion 350 and the proximal handle cavity 514 of the proximal handle portion 352. Additionally, the torque shuttle 604 can be constrained relative to the distal handle portion 350 and the proximal handle portion 352. That is, the torque shuttle 604 may be coupled to the handle portions in a manner that allows the torque shuttle 604 to move one or more of longitudinally or rotationally relative to the handle portions. The distal handle portion 350 can be one or more of longitudinally or rotationally movable relative to the proximal handle portion 352. For example, the distal handle portion 350 can be longitudinally and rotationally movable relative to the proximal handle portion 352. Accordingly, as the handle portions move relative to each other, the torque limiter 508 can move relative to the handle portions.

The torque shuttle 604 can be rotationally movable relative to the distal handle portion 350. In an embodiment, the distal handle portion 350 includes a pair of axial constraints 622 positioned longitudinally on each side of the torque shuttle 604. For example, the axial constraints 622 can include a distal constraint located distal to the torque shuttle 604 and a proximal constraint located proximal to the torque shuttle 604. The constraints can be ribs, transverse walls, etc., which extend radially inward from the distal handle portion wall, and can define a circumferential groove within when the torque shuttle 604 can spin or rotate freely about the central axis 620. The torque shuttle 604 can spin, for example, in response to relative rotation between the proximal handle portion 352 and the distal handle portion 350. More particularly, the torque shuttle 604 can be mounted on a proximal handle wall 624 that spins as the proximal handle portion rotates. Accordingly, an operator can rotate the proximal handle portion 352 to apply a torque from the proximal handle wall 624 to the torque shuttle 604 to cause the torque shuttle 604 to rotate within the circumferential groove relative to the distal handle portion 350.

The torque shuttle 604 can be longitudinally fixed relative to the distal handle portion 350. The axial constraints 622 of the distal handle portion 350 can be integrally formed with, e.g., molded into, the distal handle portion 350. The fixed features can constrain axial movement of the torque shuttle 604. For example, the torque shuttle 604 may bump into the axial constraints 622, and the constraints can limit further longitudinal movement of the torque shuttle 604. Accordingly, longitudinal movement between the torque shuttle 604 and the distal handle portion 350 can be limited.

The torque shuttle 604 can be longitudinally movable relative to the proximal handle portion 352. As described above, the torque shuttle 604 can be mounted on the proximal handle wall 624 of the proximal handle portion 352. The proximal handle portion 352 is shown in cross section in FIG. 6. In other words, a first half of the proximal handle portion 352 is shown. In an embodiment, a second half of the proximal handle portion 352 is a mirror image of the first half. Accordingly, when the first half and second half or assembled, the proximal handle wall 624 of the first half faces a proximal handle wall 624 of the second half. The facing walls can be interior walls of an axial slot 630. The axial slot 630 can have a distal stop 632 and a proximal stop 634 that limits longitudinal movement of the torque shuttle 604. More particularly, the torque shuttle 604 can slide over the proximal handle wall 624 between the distal stop 632 and the proximal stop 634. The sliding movement between the torque shuttle 604 and the proximal handle portion 352 may occur when an operator pushes or pulls on the proximal handle portion 352. The operator may push the proximal handle portion 352 to undock the biostimulator 100 from the docking cap 320. By contrast, the operator may pull the proximal handle portion 352 to dock the biostimulator 100 within the docking cap 320. When the operator pushes on the proximal handle portion 352, it can advance within the distal handle cavity 512, and as the handle 302 portion advances, the torque shuttle 604 can slide backward in the axial slot 630. By contrast, when the operator pulls on the proximal handle portion 352, it can retract within the distal handle cavity 512, and as the handle 302 portion retracts, the torque shuttle 604 can slide forward in the axial slot 630. Accordingly, the torque shuttle 604 can move longitudinally relative to the proximal handle portion 352 over a length of the slot, while remaining longitudinally fixed relative to the distal handle portion 350.

The torque shuttle 604 can be rotationally fixed relative to the proximal handle portion 352. The slot 630 of the proximal handle portion 352 can constrain rotational movement between the torque shuttle 604 and the proximal handle portion 352. For example, a width of the slot, e.g., a distance between the apposed proximal handle wall 624 faces, may be slightly larger than a width of a portion of the torque limiter 508 that extends through the slot. That is, the torque limiter 508 may be in a sliding fit within the slot, however, transverse movement between the torque limiter 508 and the proximal handle portion 352 can be limited. When the operator rotates the proximal handle portion 352, it can cause proximal handle portion 352 to spin about the central axis 620 relative to the distal handle portion 350. While the torque shuttle 604 may spin relative to the distal handle cavity 512 within the circumferential groove, it can remain rotationally fixed relative to the proximal handle portion 352 as the proximal handle wall 624 applies torque to the torque shuttle 604.

To summarize the relative movements of the torque shuttle 604 and the handle 302, the torque shuttle 604 (and the torque shaft 504) can rotate freely and remain longitudinally fixed relative to the distal handle portion 350, and by contrast, the torque shuttle 604 (and the torque shaft 504) can move longitudinally and remain rotationally fixed relative to the proximal handle portion 352. These movements may be accompanied by forces or torque applied to the torque shuttle 604. For example, longitudinal movement of the torque shuttle 604 can be constrained by axial forces applied to the torque shuttle 604 by the axial constraints 622. Similarly, rotational movement of the torque shuttle 604 can be caused by torque applied to the torque shuttle 604 by rotation of the proximal handle portion 352. Whether the rotational torque is transmitted from the torque shuttle 604 to the torque puck 602 (and the torque shaft 504) depends on the function of the torque limiter 508. More particularly, the torque limiter 508 controls relative motion between the handle portions and the torque shaft 504.

Relative movement between the torque shuttle 604 and the torque puck 602 can be modulated by the slip mechanism 606, and more particularly, the slip mechanism 606 can control an amount of torque that is transferable from the torque shuttle 604 to the torque puck 602. Accordingly, the slip mechanism 606 controls the amount of torque that is transferable from the proximal handle portion 352 to the docking cap 320 and/or the biostimulator 100 that is attached to the docking cap 320. By controlling the amount of torque that can be transferred through the system, component failures related to exceeding maximum torque values may be reduced. The torque limit that is imposed by the slip mechanism 606 may be based on a resistance torque at the docking cap 320. For example, when the resistance torque applied to the docking cap 320 by, e.g., ingrown tissue, exceeds the torque limit of the slip mechanism 606, the slip mechanism 606 can allow the torque puck 602 to slip rotationally relative to the torque shuttle 604. The resistance torque can be in a opposite direction to the drive torque applied to the docking cap 320 by the proximal handle portion 352 via the torque shaft 504, and thus, as the slip mechanism 606 slips, torque built up in the system by the sum of the resistance torque and the drive torque can be limited. Examples of slip mechanisms 606 that can limit torque build-up in the biostimulator transport system 300 are described below. In each of the embodiments, the torque puck 602 and the torque shuttle 604 rotate together when the resistance torque is below the torque threshold. By contrast, the torque puck 602 slips rotationally relative to the torque shuttle 604 when the resistance torque at the docking cap 320 is above the torque threshold.

Figure 7:
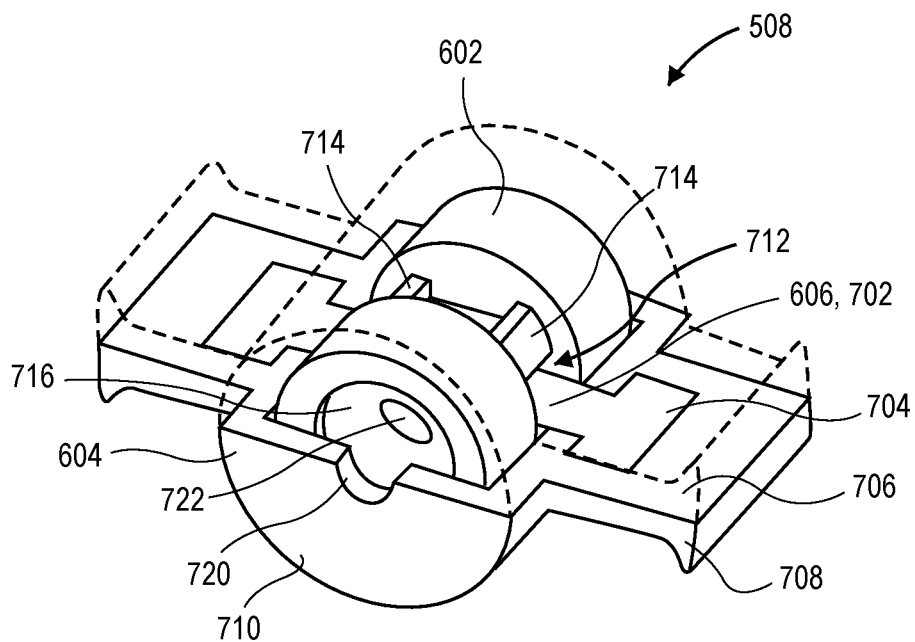
FIG. 7 is a perspective view of a torque limiter having a flat spring, in accordance with an embodiment.

Referring to FIG. 7, a perspective view of a torque limiter having a flat spring is shown in accordance with an embodiment. The slip mechanism 606 of the torque limiter 508 can include a flat spring 702. The flat spring 702 can be fixed to one of the torque puck 602 or the torque shuttle 604. For example, the flat spring 702 may have a radially outward tab 704 that is fixed to the torque shuttle 604. In an embodiment, the tab 704 is sandwiched between an upper wing 706 of an upper half of the torque shuttle 604 (shown in phantom) and the lower wing 708 of a lower half of the torque shuttle 604. The wings can extend radially outward from a cylindrical body of the torque shuttle 604, e.g., through the axial slot 630 of the proximal handle portion 352.

In an embodiment, the flat spring 702, which can be fixed to one of the torque puck 602 or the torque shuttle 604, can engage a groove 712 in the other of the torque puck 602 or the torque shuttle 604. The flat spring 702 can extend radially inward from the tab 704, which is mounted on the wings of the torque shuttle 604, toward an inner edge. The inner edge can be located within the groove 712 of the torque puck 602. More particularly, the torque puck 602 can have several radial teeth 714 distributed about a circumference of the puck, and the groove 712 can be between the teeth. The flat spring 702 can extend into the groove 712 between the teeth such that the inner edge interferes with the radial teeth 714 when the torque puck 602 spins relative to the torque shuttle 604. The interference between the flat spring 702 and the radial teeth 714 can limit rotation of the torque puck 602 relative to the torque shuttle 604.

The torque puck 602 can be fixed to the torque shaft 504, e.g., by a resistance weld, a laser weld, etc. The torque shaft 504 can extend through a distal and proximal wall in the torque shuttle 604, e.g., through a shuttle channel 720, and through an interior of the torque puck 602, e.g., through a puck channel 722. In an embodiment, an interior of the torque puck 602 is sealed from a region distal to the torque puck 602, e.g., between the torque puck 602 and the distal shuttle wall of the torque shuttle 604. Accordingly, an o-ring 716 can be positioned between a distal end of the torque puck 602 and a proximal face of the distal wall of the torque shuttle 604. Similarly, an o-ring 716 can be positioned between a proximal end of the torque puck 602 and a distal face of the proximal wall of the torque shuttle 604. The o-ring 716 can seal against the torque puck 602 along an outer radius, and can seal against the torque shaft 504 (not shown) along an inner radius. Thus, the o-ring 716 can prevent ingress or egress of fluids between an interior of the torque puck 602 and the area outside of the torque puck 602.

Figure 8:
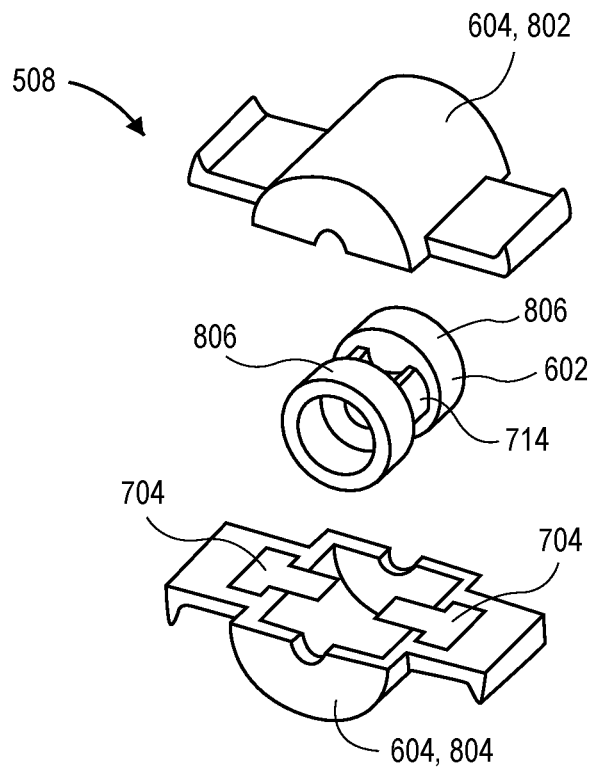
FIG. 8 is an exploded view of a torque limiter having a flat spring, in accordance with an embodiment.

Referring to FIG. 8, an exploded view of a torque limiter having a flat spring is shown in accordance with an embodiment. The exploded view illustrates that torque shuttle 604 can have an upper shuttle half 802 and a lower shuttle half 804. The upper shuttle half 802 is shown in phantom in FIG. 7 to reveal the interior components of the torque limiter 508. In FIG. 8, it is apparent that the shuttle halves form respective portions of the shuttle body and wings, which when combined, can form the cylindrical body containing the torque puck 602, and the wings clamping the flat springs 702. More particularly, each shuttle half can contain a semi-cylindrical volume that receives the torque puck 602. The torque puck 602 can have distal and proximal puck hubs 806 that have circular profiles to allow the puck hubs 806 to rotate within the semi-cylindrical volume of the torque shuttle 604. Such rotation, however, is resisted by the engagement of the slip mechanism 606 to the radial teeth 714 of the torque puck 602.

Figure 9:
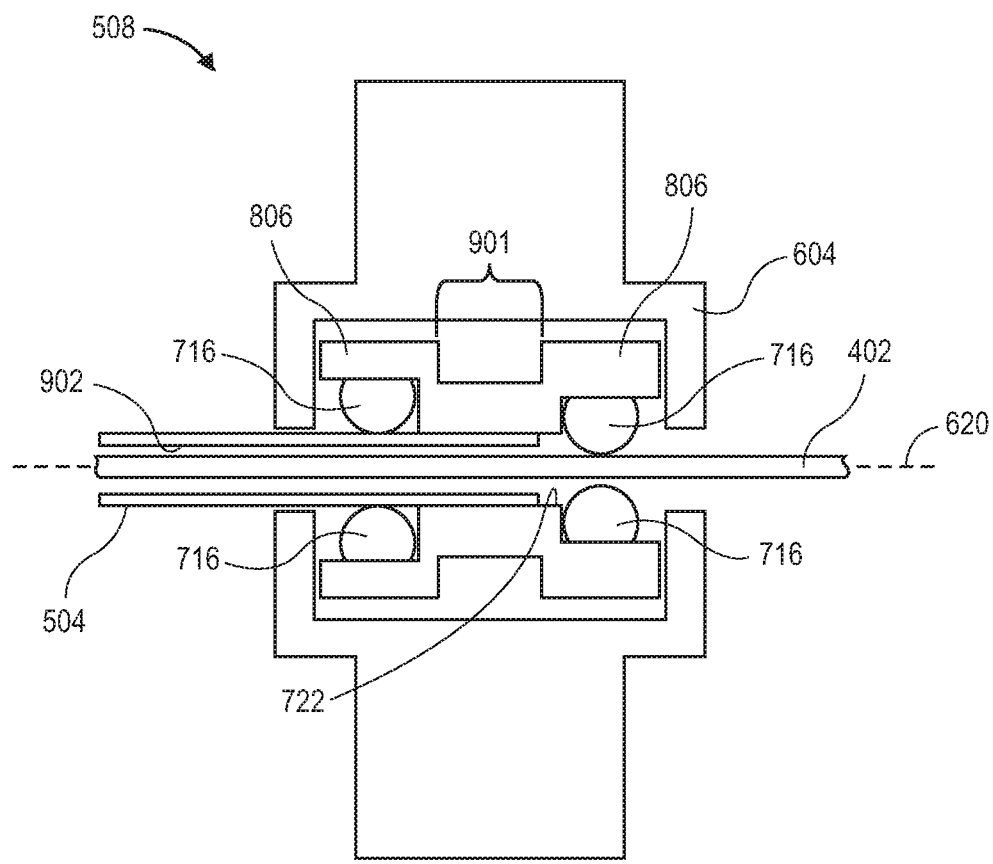
FIG. 9 is a cross-sectional top view of a torque limiter having a flat spring, in accordance with an embodiment.

Referring to FIG. 9, a cross-sectional top view of a torque limiter having a flat spring is shown in accordance with an embodiment. In cross-section, the body of the torque shuttle 604 has a rectangular profile surrounding the cylindrical shuttle volume. The distal and the proximal puck hubs 806 can fit within the shuttle volume. In an embodiment, a central section 901 of the torque puck 602 extends between the distal and the proximal puck hubs 806. The central section 901 can include the radial teeth 714 that extend radially outward from the central axis 620.

In an embodiment, the torque shaft 504 extends into the torque puck 602, e.g., through the puck channel 722. The torque shaft 504 can be joined to the torque puck 602 at a distal and/or proximal edge of the puck channel 722, or within the puck channel 722, e.g., to an internal surface surrounding the puck channel 722. The torque shaft 504 includes a shaft lumen 902, and as described above, the snare 402 can extend through shaft lumen 902 from a location distal to the torque shuttle 604, through the torque shuttle 604 and the torque puck 602, to a location proximal to the torque shuttle 604.

Figure 10:
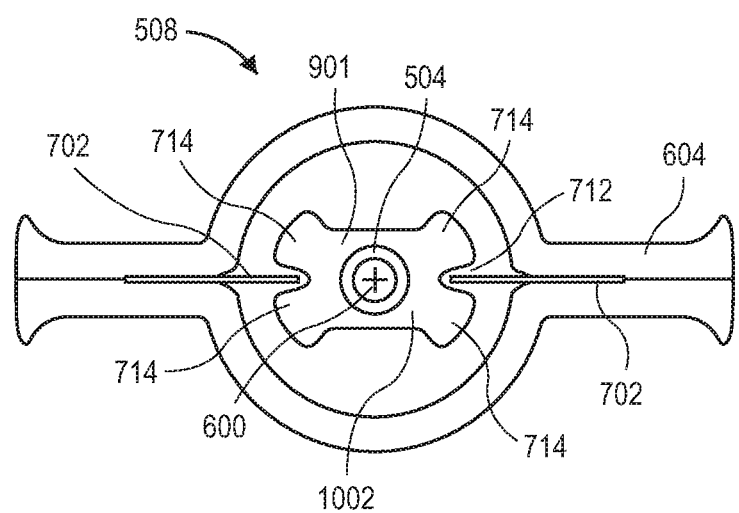
FIG. 10 is a cross-sectional end view of a torque limiter having a flat spring, in accordance with an embodiment.

Referring to FIG. 10, a cross-sectional end view of a torque limiter having a flat spring is shown in accordance with an embodiment. The torque limiter 508 can have one or more flat springs 702. The flat spring(s) 702 can extend into respective grooves 712 between the radial teeth 714. The radial teeth 714 can extend radially outward from the central axis 620. More particularly, the radial teeth 714 can extend radially outward from a central section 901 of the torque puck 602. The radial teeth 714 can have gear-shaped profiles, radial fin profiles, or any other profiles that provide radial protrusions between which grooves 712 are defined. The flat spring 702 can fit within the groove 712 to limit rotational movement to the width of the groove 712, unless sufficient torque is applied to displace the flat spring 702 from of the groove 712.

In an embodiment, the flat spring 702 has a rigidity that tunes a maximum torque that can be built up within the torque limiter 508 before the torque puck 602 slips relative to the torque shuttle 604. The flat spring 702 can be formed from spring steel, nickel titanium, polymers, or other biocompatible materials that are sufficiently stiff to resist bending when the resistance torque is applied to the inner edges of the flat spring 702 by the torque shaft 504.

The stiffness of the flat spring 702 determines the torque that can be built up in the system before the radial teeth 714 bend the flat spring 702 out of the groove 712 and allow the torque puck 602 to rotate relative to the torque shuttle 604. More particularly, the torque threshold of the resistance torque can be predetermined based on a stiffness of the flat spring 702. To rotate the torque shaft 504, the proximal handle portion 352 can be twisted by an operator to transfer torque through the flat spring 702 to the radial teeth 714. Torque is transferred to the torque puck 602 and the torque shaft 504 until the torque built up in the torque shaft 504 reaches the set level. When the set level is reached, e.g., when the resistance torque on the torque shaft 504 is equal to or greater than the torque threshold, the flat spring 702 is deflected by the radial teeth 714 and will slip from one groove 712 to a next groove 712 in the sequence of grooves around the central section 901. When the flat spring 702 ratchets to the next groove, the torque shaft 504 will slip rotationally relative to the proximal handle portion 352. Excessive torque buildup is thereby prevented.

A resistance element, such as flat spring 702 within groove 712, is only one example of the slip mechanisms 606 that can limit torque transfer between the torque shuttle 604 and the torque puck 602. Other examples follow.

Figure 11:
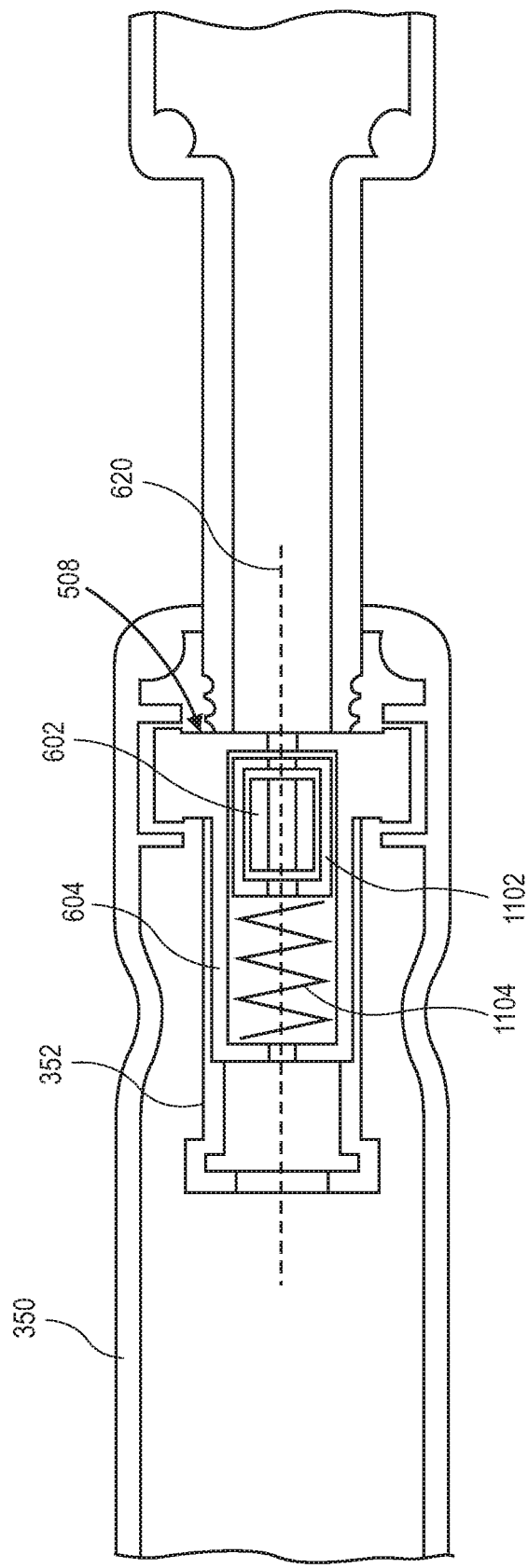
FIG. 11 is a cross-sectional side view of a biostimulator transport system handle, in accordance with an embodiment.

Referring to FIG. 11, a cross-sectional side view of a biostimulator transport system handle is shown in accordance with an embodiment. The torque limiter 508 can include the torque puck 602 and the torque shuttle 604, as described above. In an embodiment, the slip mechanism 606 includes an inner shuttle 1102 that contains the torque puck 602. For example, the inner shuttle 1102 can have an internal volume sized and shaped to receive an exterior of the torque puck 602. The internal volume can be polyhedral, for example, and the torque puck 602 may have a similar polyhedral exterior that fits within and conforms to the interior of the torque puck 602.

In an embodiment, the inner shuttle 1102 is longitudinally movable relative to the torque shuttle 604. For example, the inner shuttle 1102 may slide longitudinally along the central axis 620 within an inner volume of the torque shuttle 604. Similarly, the inner shuttle 1102 may rotate about the central axis 620 within the inner volume of the torque shuttle 604. The extent to which the inner shuttle 1102 moves relative to the torque shuttle 604 may, however, be constrained. For example, the slip mechanism 606 can include a bias element 1104, such as a compression spring, that acts between the torque shuttle 604 and the inner shuttle 1102. The bias element 1104 can be coupled to the inner shuttle 1102 and the torque shuttle 604 to bias the inner shuttle 1102 toward one side of the torque shuttle 604, e.g., toward a proximal shuttle wall. Accordingly, the bias element 1104 can limit longitudinal movement of the inner shuttle 1102 based on the spring constant of the bias element 1104. When the bias element 1104 biases the inner shuttle 1102 toward the shuttle wall, an outer face of the inner shuttle 1102 can press against the shuttle wall of torque shuttle 604. The contacting faces can provide a clutching mechanism. For example, the pressure between the components can generate friction that limits rotation of the inner shuttle 1102 relative to the torque shuttle 604. Accordingly, the bias element 1104 can limit rotational movement of the inner shuttle 1102 by generating friction or interference that limits rotation of the inner shuttle 1102 relative to the torque shuttle 604.

Figure 12:
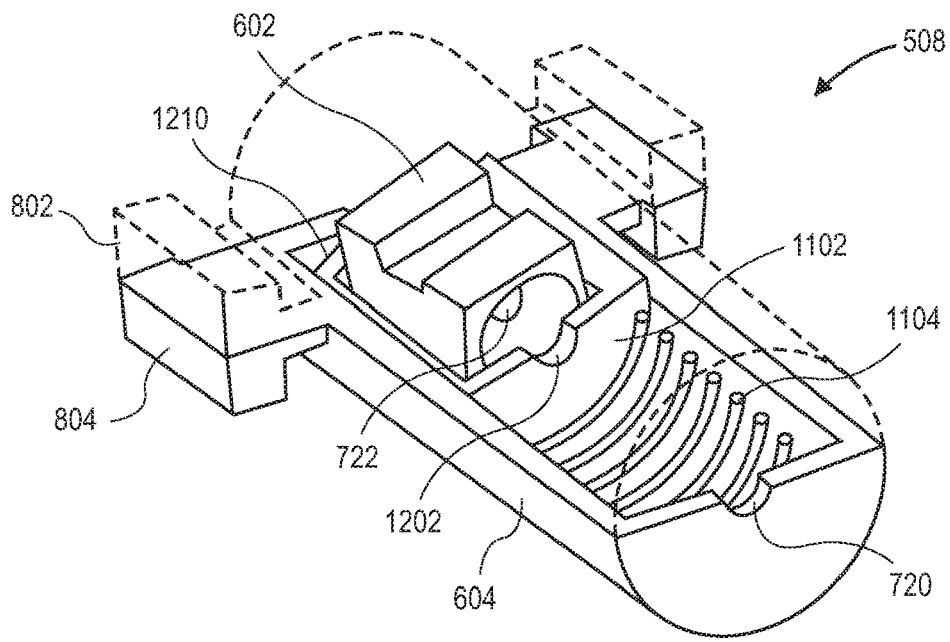
FIG. 12 is a perspective view of a torque limiter having a clutch assembly, in accordance with an embodiment.

Referring to FIG. 12, a perspective view of a torque limiter having a clutch assembly is shown in accordance with an embodiment. The upper shuttle half 802 is shown in phantom to increase the visibility of the internal components of the torque limiter 508. The torque shaft 504 is omitted from the view, however, it will be appreciated that the torque shaft 504 can extend through the shuttle channel 720 and the puck channel 722 to connect to the puck via a weld, an adhesive bond, etc. The inner shuttle 1102 can include an inner shuttle channel 1202 aligned with the puck channel 722 and the shuttle channel 720 along the central axis 620. Accordingly, the torque shaft 504 and the snare 402 can extend distally through the torque limiter 508 toward the distal end of the biostimulator transport system 300. As shown, the bias element 1104 can apply a separating force between a distal face of the inner shuttle 1102 and the distal shuttle wall. Accordingly, the inner shuttle 1102 can be biased in a rearward direction to force a proximal face of the inner shuttle 1102 against a distal interior face of the proximal shuttle wall at a clutching interface 1210.

Figure 13:
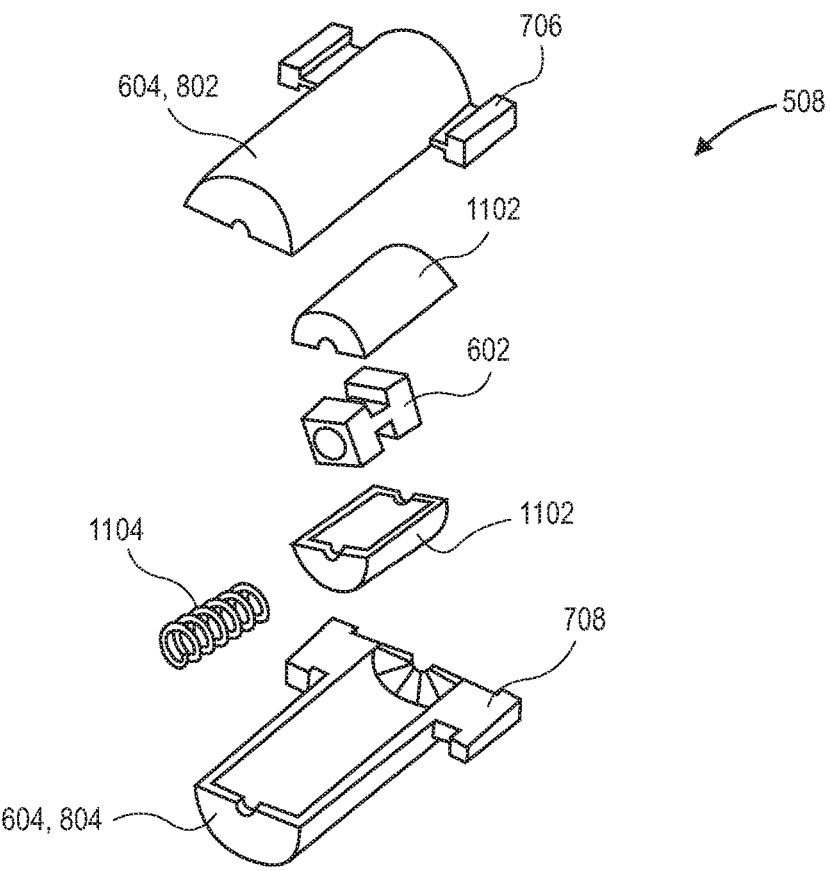
FIG. 13 is an exploded view of a torque limiter having a clutch assembly, in accordance with an embodiment.

Referring to FIG. 13, an exploded view of a torque limiter having a clutch assembly is shown in accordance with an embodiment. The exploded view reveals that the upper shuttle half 802 and the lower shuttle half 804 have geometries similar to the geometries of the torque shuttle 604 described above. For example, an internal volume of the torque shuttle 604 may be cylindrical. Also, the shuttle can have wings extending laterally to interfere with the proximal handle slot. An exterior profile of the inner shuttle 1102 may be cylindrical to conform to the internal volume of the torque shuttle 604, and to allow the inner shuttle 1102 to slide smoothly against the interior surface of the torque shuttle 604 that defines the internal volume.

The inner shuttle 1102, like the torque shuttle 604, can have an upper and a lower half. When assembled, the halves can form an internal volume. The internal volume of the inner shuttle 1102 may receive the torque puck 602. An exterior profile of the torque puck 602 may conform to an interior surface of the inner shuttle 1102 that defines the internal volume. For example, the exterior profile of the torque puck 602 can be polyhedral, e.g., a block, an I-beam shape, etc. The interior surface of the inner shuttle 1102 can conform to the shape. Accordingly, the torque puck 602 can fit tightly within the inner shuttle 1102 and both longitudinal and rotational movement of the torque puck 602 relative to the inner shuttle 1102 may therefore be constrained and/or prevented.

Figure 14:
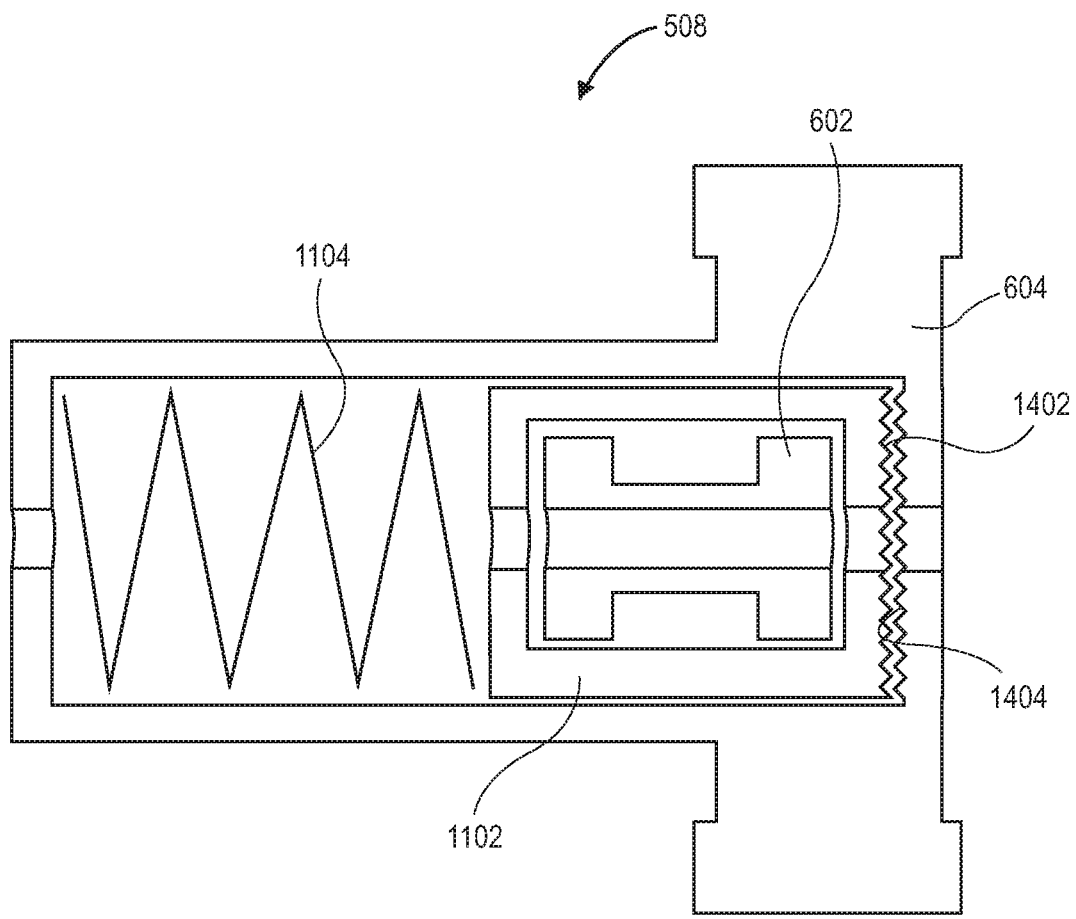
FIG. 14 is a cross-sectional top view of a torque limiter having a clutch assembly, in accordance with an embodiment.

Referring to FIG. 14, a cross-sectional top view of a torque limiter having a clutch assembly is shown in accordance with an embodiment. The slip mechanism 606 can include several clutching surfaces that are apposed to one another. In an embodiment, the inner shuttle 1102 has an inner clutch face 1402 apposed to an outer clutch face 1404 of the torque shuttle 604. The bias element 1104, which is coupled to the inner shuttle 1102 and the torque shuttle 604, can press the inner clutch face 1402 against the outer clutch face 1404 to generate friction between the inner shuttle 1102 in the torque shuttle 604. Accordingly, the clutching surfaces can resist rotational movement relative to one another and can transmit torque from the torque shuttle 604 to the inner shuttle 1102, and thus, to the torque puck 602 and the torque shaft 504.

Torque transmission between the torque shuttle 604 and the inner shuttle 1102 can be controlled through the spring constant of the bias element 1104 and/or through the clutch surface design. For example, increasing the spring constant can cause the bias element 1104 to generate more pressure between the inner shuttle 1102 and the torque shuttle 604, and therefore, can increase the friction and the torque that may be transmitted between the shuttles before the inner shuttle 1102 will slip relative to the torque shuttle 604. Similarly, the surface shape and finish can be altered to tune the friction between the shuttles. Accordingly, the slip torque can be controlled by one or more of the pressure generated between the clutch faces by the bias element 1104 or the friction and/or interlocking between the surfaces.

In an embodiment, the inner clutch face 1402 and the outer clutch face 1404 are planar surfaces. The planar surfaces can be smooth or rough. As the planar surfaces become rougher, the friction coefficient between the surfaces can increase. It will be appreciated that, as the friction coefficient increases, the friction and the maximum torque transmitted between the clutching surfaces increases. Accordingly, the slip torque between the clutch faces can be increased by making the planar surfaces rougher.

Figure 15:
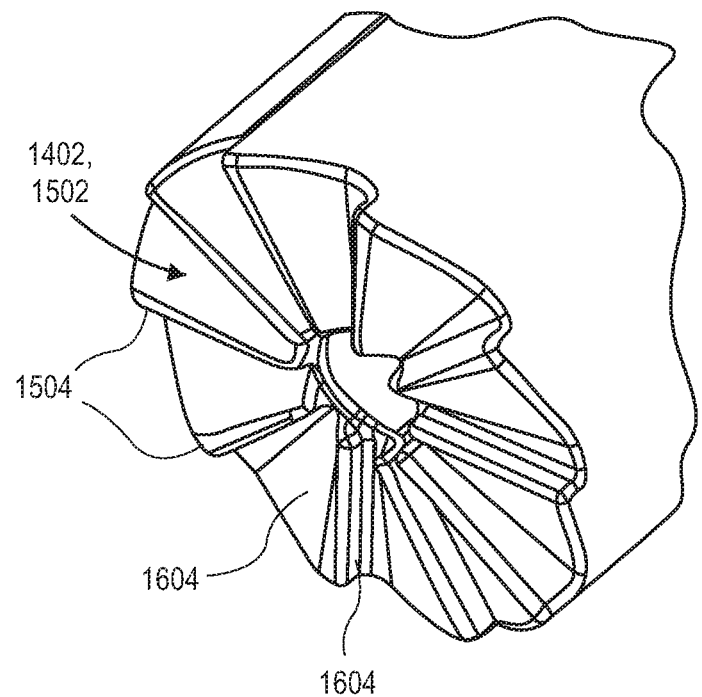
FIG. 15 is a perspective view of an inner clutch face, in accordance with an embodiment.
Figure 16:
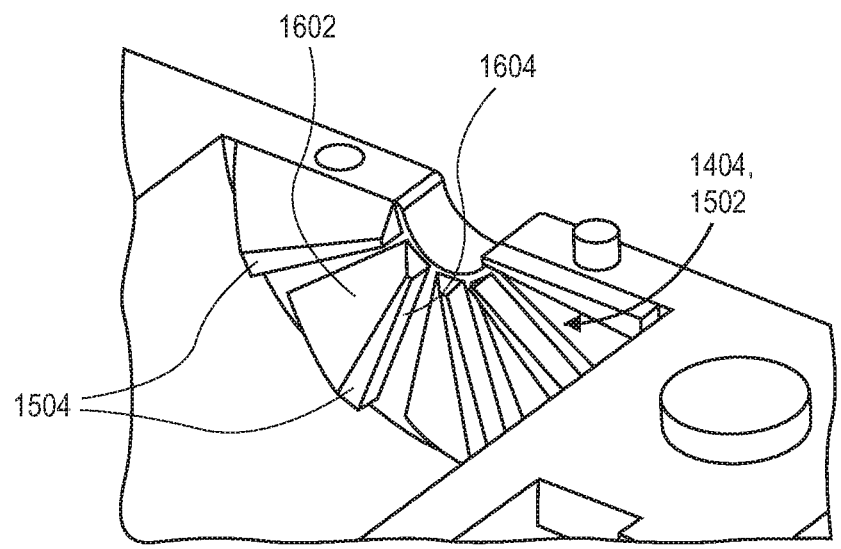
FIG. 16 is a perspective view of an outer clutch face, in accordance with an embodiment.

Referring to FIGS. 15-16, perspective views of an inner clutch face and an outer clutch face are shown in accordance with an embodiment. The clutching surfaces may be non-planar. For example, the inner clutch face 1402 and the outer clutch face 1404 can be nonplanar meshing surfaces 1502.

In an embodiment, the nonplanar meshing surfaces 1502 may have wavelike contours that interface with each other. For example, a transverse plane orthogonal to the central axis 620 may intersect both of the clutching surfaces when the clutching surfaces are engaged. Accordingly, the wavelike contours can interfere with each other. Interference between the contours can cause positive engagement that transmits force, in addition to frictional loads between the surfaces. Thus, the nonplanar outer clutch face 1404 of the torque shuttle 604 can transmit torque to the nonplanar inner clutch face 1402 of the inner shuttle 1102, and vice versa. The slip torque of the non-planar meshing surfaces 1502 may be greater than the slip torque of the planar meshing surfaces.

The non-planar surfaces of the clutching faces may have smooth contours, or alternatively, the clutching surfaces can have abrupt surfaces. For example, the inner shuttle 1102 and the outer shuttle can interface through a gear plate. In an embodiment, the clutching surfaces of the non-planar meshing surfaces 1502 include one or more clutch dogs 1504. The clutch dogs 1504 can be axial protrusions extending from respective clutch faces that interfere with one another when the clutching surfaces are in contact. For example, each clutch dog 1504 can be a tooth of a gear plate, and the teeth can engage each other when the bias element 1104 presses the inner clutch face 1402 against the outer clutch face 1404.

An example of the clutch dogs 1504 being gear teeth is shown in FIGS. 15-16, however, it is noted that such teeth profile are provided by way of example and not limitation. Each gear tooth of the illustrated gear teeth has a sloped surface 1602 oblique to the central axis 620 direction, and a longitudinal surface 1604 parallel to the central axis 620 direction. When engaged, the sloped surfaces 1602 can ride over each other to allow surfaces to slip relative to each other when sufficient resistance torque is encountered. By contrast, the longitudinal surfaces 1604, when engaged, will interfere directly and may not be able to slide relative to each other. Accordingly, the illustrated tooth design provides one-way clutching because the inner shuttle 1102 can slip relative to the torque shuttle 604 in a first rotational direction (the direction along which the sloped surfaces 1602 slide over each other) and cannot slip relative to the torque shuttle 604 in a second rotational direction (the direction of contact between the longitudinal surfaces 1604).

In an embodiment, the clutch dogs 1504 may allow for slipping in both rotational directions. For example, the non-planar meshing surfaces 1502 can include clutch dogs 1504 that have two sloped surfaces 1602 meeting at an apex. The apex can be a distalmost point along the clutch dog 1504. The sloped surfaces 1602 can slide over each other, and since the slopes extend in both directions, the clutch dogs 1504 can slide relative to each other in both directions. A torque threshold at which the sliding occurs can be controlled by a slope, e.g., a height and width, of the sloped surfaces 1602. Accordingly, the slip torque of the torque limiter 508 can be controlled through the clutch dog design. More particularly, the clutch dogs 1504 of the torque shuttle 604 can drive the clutch dogs 1504 of the inner shuttle 1102 until sufficient resistance torque is applied to the torque shaft 504. When the resistance torque is encountered, the clutch dogs 1504 can slide over each other, causing the bias element 1104 to compress and allowing the inner clutch face 1402 to slip relative to the outer clutch face 1404. More particularly, the spring force of the bias element 1104 can be overcome, allowing the torque shuttle 604 and the inner shuttle 1102 to turn independently from each other until the torque in the system is reduced. When the slip mechanism slips, the likelihood of excessive torque build up in the system is reduced.

Figure 17:
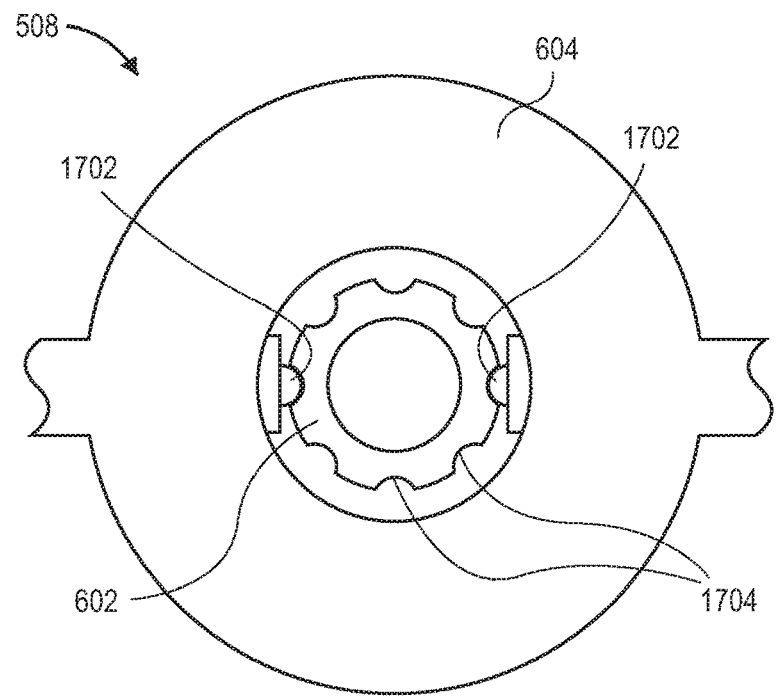
FIG. 17 is an end view of a torque limiter having a ball plunger, in accordance with an embodiment.

Referring to FIG. 17, an end view of a torque limiter having a ball plunger is shown in accordance with an embodiment. The slip mechanism 606 may include a feature on the torque shuttle 604 that engages a corresponding feature on the torque puck 602. For example, the slip mechanism 606 can include one or more ball plungers 1702 that are fixed to one of the torque puck 602 or the torque shuttle 604, and that engage a corresponding recess 1704 in the other of the torque puck 602 or the torque shuttle 604. The ball plunger(s) 1702 can transfer torque from the torque shuttle 604 to the torque puck 602. When the torque threshold is reached, the ball plungers 1702 can slip relative to the engaged recesses 1704 to allow the torque puck 602 and the torque shaft 504 to release built up torque within the system.

In an embodiment, a ball plunger 1702 is mounted on or otherwise fixed relative to the torque shuttle 604. The ball plunger 1702 can engage the corresponding recess 1704 on an outer surface of the torque puck 602. For example, the outer surface of the torque puck 602 can be a knurled surface having recesses 1704 radially inward from an outermost location on the surfaces. When a ball of the ball plunger 1702 extends into the recess 1704, it forms an interlock between the torque shuttle 604 and the torque puck 602. More particularly, torque can be transmitted from the torque shuttle 604 to the torque puck 602 via the interference between the ball and the recess 1704. An amount of interference can be controlled, e.g., by tuning a depth of the recess 1704 or a spring constant of a spring in the ball plunger 1702 that forces the ball into the recess 1704. By tuning this interference, the slip torque of the torque limiter 508 may be controlled. Accordingly, the torque limiter 508 can be set to transmit torque from the torque shuttle 604 to the torque puck 602 until the resistance torque at the docking cap 320 exceeds the torque threshold.

Figure 18:
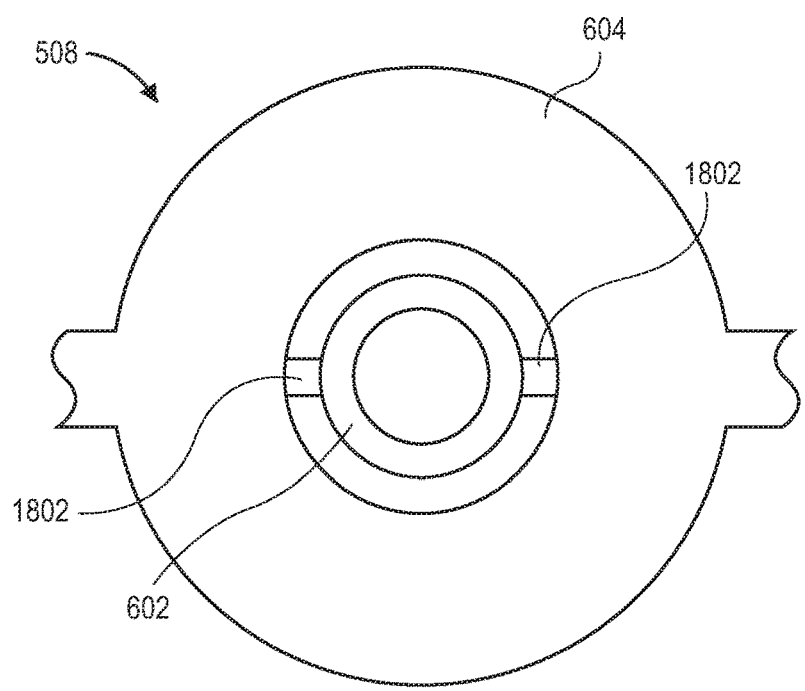
FIG. 18 is an end view of a torque limiter having a shear pin, in accordance with an embodiment.

Referring to FIG. 18, an end view of a torque limiter having a shear pin is shown in accordance with an embodiment. The slip mechanism 606 may include an attachment between the torque shuttle 604 and the torque puck 602. For example, the slip mechanism 606 can include one or more shear pins 1802 that are fixed to and extend between the torque puck 602 and the torque shuttle 604. The shear pin(s) 1802 can transfer torque from the torque shuttle 604 to the torque puck 602 to drive rotation of the torque shaft 504. When the torque threshold is reached, the shear pins 1802 can break and allow the torque puck 602 and the torque shaft 504 to release built up torque in the system.

The shear pins 1802 can be independent components that are assembled into the torque shuttle 604 and the torque puck 602, or alternatively, the shear pins 1802 may be integrally formed with the torque limiter components, e.g., in a plastic molding process. In an embodiment, the shear pins 1802 are polymeric and have a cross-sectional area such that shear developed by the application of the predetermined resistance torque causes the shear pins 1802 to fail. The failure point can be tuned by adjusting the material characteristics and/or the cross-sectional area of the shear pins 1802.

By tuning the failure point of the shear pins 1802, the slip torque of the torque limiter 508 may be controlled. Accordingly, the torque limiter 508 can be set to transmit torque from the torque shuttle 604 to the torque puck 602 until the shear pins 1802 fail under the resistance torque at the docking cap 320. The resistance torque can cause failure when the torque equals or exceeds the torque threshold.

It will be appreciated that the torque limiter 508 may, as in the case of FIG. 18, be a destructive, one-time use limiter. More particularly, when the torque threshold is exceeded and the shear pins 1802 fail, the operator may be unable to transmit torque from the proximal handle portion 352 to the docking cap 320. Accordingly, the operator may replace the failed biostimulator transport system 300 with a new biostimulator transport system 300.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A torque shaft assembly, comprising:
    an elongated flexible tubular member;
    a docking cap coupled to the elongated flexible tubular member, wherein the docking cap has a docking cavity to receive an attachment feature of a biostimulator;
    a torque shaft extending from a proximal shaft end distally through the elongated flexible tubular member to a distal shaft end coupled to the docking cap; and
    a torque limiter including a torque puck mounted on the proximal shaft end of the torque shaft, a torque shuttle rotationally coupled to the torque puck, and a slip mechanism between the torque puck and the torque shuttle to allow the torque puck to slip relative to the torque shuttle based on a resistance torque at the docking cap.

2. The torque shaft assembly of claim 1, wherein the torque puck and the torque shuttle rotate together when the resistance torque is below a torque threshold, and wherein the torque puck slips rotationally relative to the torque shuttle when the resistance torque at the docking cap is above the torque threshold.

3. The torque shaft assembly of claim 1, wherein the slip mechanism includes a flat spring fixed to one of the torque puck or the torque shuttle, and wherein the flat spring engages a groove in the other of the torque puck or the torque shuttle.

4. The torque shaft assembly of claim 3, wherein the torque puck includes a plurality of radial teeth, and wherein the flat spring is fixed to the torque shuttle and extends into the groove between the plurality of radial teeth.

5. The torque shaft assembly of claim 1, wherein the slip mechanism includes an inner shuttle containing the torque puck, wherein the inner shuttle has an inner clutch face apposed to an outer clutch face of the torque shuttle, and wherein the slip mechanism includes a bias element coupled to the inner shuttle and the torque shuttle to press the inner clutch face against the outer clutch face.

6. The torque shaft assembly of claim 5, wherein the inner shuttle is longitudinally movable relative to the torque shuttle.

7. The torque shaft assembly of claim 5, wherein the inner clutch face and the outer clutch face are non-planar meshing surfaces.

8. The torque shaft assembly of claim 7, wherein the non-planar meshing surfaces include one or more clutch dogs.

9. The torque shaft assembly of claim 1, wherein the slip mechanism includes a ball plunger fixed to one of the torque puck or the torque shuttle, and wherein the ball plunger engages a recess in the other of the torque puck or the torque shuttle.

10. The torque shaft assembly of claim 1, wherein the slip mechanism includes a shear pin fixed to and extending between the torque puck and the torque shuttle.

11. A biostimulator transport system, comprising:
    an elongated flexible tubular member;
    a docking cap coupled to the elongated flexible tubular member, wherein the docking cap has a docking cavity to receive an attachment feature of a biostimulator
    a torque shaft extending from a proximal shaft end distally through the elongated flexible tubular member to a distal shaft end coupled to the docking cap;
    a handle having a handle cavity; and
    a torque limiter in the handle cavity, wherein the torque limiter includes a torque puck mounted on the proximal shaft end of the torque shaft, a torque shuttle coupled to the handle and the torque puck, and a slip mechanism between the torque shuttle and the torque puck to allow the torque shaft to rotate relative to the handle based on a resistance torque on the torque shaft.

12. The biostimulator transport system of claim 11, wherein the handle includes a distal handle portion longitudinally and rotationally movable relative to a proximal handle portion, wherein the torque shuttle is longitudinally fixed and rotationally movable relative to the distal handle portion, and wherein the torque shuttle is longitudinally movable and rotationally fixed relative to the proximal handle portion.

13. The biostimulator transport system of claim 12, wherein the handle cavity includes a distal handle cavity within the distal handle portion and a proximal handle cavity within the proximal handle portion, and wherein the torque shuttle is contained within the distal handle cavity and the proximal handle cavity.

14. The biostimulator transport system of claim 11, wherein the slip mechanism includes a flat spring fixed to one of the torque puck or the torque shuttle, and wherein the flat spring engages a groove in the other of the torque puck or the torque shuttle.

15. The biostimulator transport system of claim 11, wherein the slip mechanism includes an inner shuttle containing the torque puck, wherein the inner shuttle has an inner clutch face apposed to an outer clutch face of the torque shuttle, and wherein the slip mechanism includes a bias element coupled to the inner shuttle and the torque shuttle to press the inner clutch face against the outer clutch face.

16. The biostimulator transport system of claim 11, wherein the slip mechanism includes a ball plunger fixed to one of the torque puck or the torque shuttle, wherein the ball plunger engages a recess in the other of the torque puck or the torque shuttle.

17. The biostimulator transport system of claim 11, wherein the slip mechanism includes a shear pin fixed to and extending between the torque puck and the torque shuttle.

18. A biostimulator retrieval system, comprising:
an elongated flexible tubular member;
a docking cap coupled to the elongated flexible tubular member, wherein the docking cap has a docking cavity to receive an attachment feature of a biostimulator;
a torque shaft extending from a proximal shaft end distally through the elongated flexible tubular member to a distal shaft end coupled to the docking cap;
a handle;
a torque limiter including a torque puck mounted on the proximal shaft end of the torque shaft, a torque shuttle coupled to the handle, and a slip mechanism between the torque shuttle and the torque puck to allow the torque shaft to rotate relative to the handle based on a resistance torque at the docking cap; and
a snare extending through the torque puck, the torque shaft, and the docking cap.

19. The biostimulator retrieval system of claim 18, wherein the snare includes a snare tube having a central lumen and one or more snare loops extending through the central lumen.

20. The biostimulator retrieval system of claim 19, wherein the torque shaft has a shaft lumen, and wherein the snare tube is longitudinally movable within the shaft lumen.

\* \* \* \* \*